(12) United States Patent
Katz et al.

(10) Patent No.: US 11,547,336 B2
(45) Date of Patent: Jan. 10, 2023

(54) APPARATUS AND METHODS FOR MONITORING A SUBJECT

(71) Applicant: Hill-Rom Services, Inc., Batesville, IN (US)

(72) Inventors: Yaniv Katz, Ra'anana (IL); Roman Karasik, Lod (IL); Zvika Shinar, Binyamina (IL); Avner Halperin, Ramat Gan (IL); Guy Meger, Tel Aviv (IL); Liat Tsoref, Tel Aviv (IL); Maayan Lia Yizraeli Davidovich, Haifa (IL)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 17/103,826

(22) Filed: Nov. 24, 2020

(65) Prior Publication Data

US 2021/0100489 A1 Apr. 8, 2021

Related U.S. Application Data

(63) Continuation of application No. 16/877,543, filed on May 19, 2020, now abandoned, which is a
(Continued)

(51) Int. Cl.
*A61B 5/00* (2006.01)
*A61B 5/18* (2006.01)
(Continued)

(52) U.S. Cl.
CPC .............. *A61B 5/18* (2013.01); *A61B 5/02* (2013.01); *A61B 5/11* (2013.01); *A61B 5/6891* (2013.01);
(Continued)

(58) Field of Classification Search
CPC .......... A61B 5/02; A61B 5/6891; A61B 5/18; A61B 5/11; A61B 5/6893; A61B 2562/0219; B60N 2/90; B60N 2/002
See application file for complete search history.

(56) References Cited

U.S. PATENT DOCUMENTS

| 5,447,161 A | 9/1995 | Blazek et al. |
| 6,217,525 B1 | 4/2001 | Medema et al. |

(Continued)

FOREIGN PATENT DOCUMENTS

| WO | 2005074361 A2 | 8/2005 |
| WO | 2006137067 A2 | 12/2006 |

(Continued)

*Primary Examiner* — Mohamed Charioui
*Assistant Examiner* — Christine Y Liao
(74) *Attorney, Agent, or Firm* — Barnes & Thornburg LLP

(57) ABSTRACT

Apparatus and methods are described for monitoring a subject. A sensor monitors the subject and generates a sensor signal in response thereto and a plurality of filters are used to filter the sensor signal using respective filter parameters. A computer processor receives the sensor signal, filters the signal with each of two or more of the filters, and in response to a quality of each of the filtered signals, selects one of the plurality of filters to filter the sensor signal. Subsequently, the computer processor detects that the subject has undergone motion, by analyzing the sensor signal, and in response thereto, filters the signal with each of two or more of the filters, and in response to a quality of each of the filtered signals, selects one of the plurality of filters to filter the sensor signal. Other applications are also described.

20 Claims, 10 Drawing Sheets

Related U.S. Application Data continuation of application No. 15/431,842, filed on Feb. 14, 2017, now abandoned.

(60) Provisional application No. 62/295,077, filed on Feb. 14, 2016.

(51) Int. Cl.
  B60N 2/90 (2018.01)
  B60N 2/00 (2006.01)
  A61B 5/02 (2006.01)
  A61B 5/11 (2006.01)

(52) U.S. Cl.
  CPC ............ A61B 5/6893 (2013.01); B60N 2/002 (2013.01); B60N 2/90 (2018.02); *A61B 2562/0219* (2013.01)

(56) References Cited

U.S. PATENT DOCUMENTS

| | | |
|---|---|---|
| 6,438,477 B1 | 8/2002 | Patterson et al. |
| 6,575,902 B1 | 6/2003 | Burton |
| 7,077,810 B2 | 7/2006 | Lange et al. |
| 7,314,451 B2 | 1/2008 | Halperin et al. |
| 8,376,954 B2 | 2/2013 | Lange et al. |
| 8,403,865 B2 | 3/2013 | Halperin et al. |
| 8,491,492 B2 | 7/2013 | Shinar et al. |
| 8,517,953 B2 | 8/2013 | Lange et al. |
| 8,585,607 B2 | 11/2013 | Klap et al. |
| 8,603,010 B2 | 12/2013 | Lange et al. |
| 8,679,030 B2 | 3/2014 | Shinar et al. |
| 8,679,034 B2 | 3/2014 | Halperin et al. |
| 8,731,646 B2 | 5/2014 | Halperin et al. |
| 8,734,360 B2 | 5/2014 | Klap et al. |
| 8,821,418 B2 | 9/2014 | Meger et al. |
| 8,840,564 B2 | 9/2014 | Pinhas et al. |
| 8,882,684 B2 | 11/2014 | Halperin et al. |
| 8,942,779 B2 | 1/2015 | Halperin et al. |
| 8,992,434 B2 | 3/2015 | Halperin et al. |
| 8,998,830 B2 | 4/2015 | Halperin et al. |
| 9,026,199 B2 | 5/2015 | Halperin et al. |
| 2003/0229289 A1* | 12/2003 | Mohler ................. A61B 5/322 600/508 |
| 2004/0061615 A1 | 4/2004 | Takashima |
| 2004/0245036 A1 | 12/2004 | Fujita et al. |
| 2006/0122663 A1 | 6/2006 | Mandell |
| 2006/0145457 A1 | 7/2006 | Prenzel et al. |
| 2006/0253238 A1 | 11/2006 | Murphy et al. |
| 2006/0255955 A1 | 11/2006 | O'Connor et al. |
| 2007/0118026 A1 | 5/2007 | Kameyama et al. |
| 2007/0118054 A1 | 5/2007 | Pinhas et al. |
| 2008/0114260 A1 | 5/2008 | Lange et al. |
| 2008/0156602 A1 | 7/2008 | Hiemenz et al. |
| 2008/0275349 A1 | 11/2008 | Halperin et al. |
| 2008/0300804 A1 | 12/2008 | Spruytte |
| 2009/0069641 A1 | 3/2009 | Cho et al. |
| 2010/0056937 A1 | 3/2010 | Imamura et al. |
| 2011/0112442 A1* | 5/2011 | Meger ................. A61B 5/4818 600/595 |
| 2011/0257555 A1* | 10/2011 | Banet ..................... A61B 5/113 600/538 |
| 2012/0029586 A1 | 2/2012 | Kumar et al. |
| 2012/0132211 A1 | 5/2012 | Halperin et al. |
| 2012/0253142 A1 | 10/2012 | Meger et al. |
| 2013/0102912 A1 | 4/2013 | Trayanova et al. |
| 2013/0245502 A1 | 9/2013 | Lange et al. |
| 2013/0251096 A1 | 9/2013 | Hiraoka |
| 2013/0310700 A1 | 11/2013 | Wiard et al. |
| 2014/0005502 A1 | 1/2014 | Klap et al. |
| 2014/0371635 A1* | 12/2014 | Shinar .................. A61B 5/1102 600/595 |
| 2015/0164433 A1 | 6/2015 | Halperin et al. |
| 2015/0164438 A1 | 6/2015 | Halperin et al. |
| 2015/0190087 A1 | 7/2015 | Shinar et al. |
| 2015/0229341 A1 | 8/2015 | Fung et al. |
| 2015/0317834 A1 | 11/2015 | Poulos et al. |
| 2015/0327792 A1 | 11/2015 | Shinar et al. |
| 2015/0342492 A1 | 12/2015 | Thakur et al. |
| 2016/0058428 A1 | 3/2016 | Shinar et al. |
| 2016/0058429 A1 | 3/2016 | Shinar et al. |
| 2016/0120466 A1 | 5/2016 | Halperin et al. |
| 2016/0234910 A1 | 8/2016 | Harada |
| 2016/0262704 A1* | 9/2016 | Min ..................... A61B 5/0245 |
| 2016/0287128 A1* | 10/2016 | Jain ...................... A61B 5/327 |
| 2017/0156614 A1 | 6/2017 | Ibez Catal |
| 2017/0156618 A1* | 6/2017 | Narasimhan ........... A61B 5/721 |
| 2018/0120425 A1* | 5/2018 | Skoglund ................ G01S 15/02 |
| 2018/0220897 A1 | 8/2018 | Meger et al. |
| 2019/0083044 A1 | 3/2019 | Halperin et al. |
| 2019/0090860 A1 | 3/2019 | Shinar et al. |
| 2019/0183353 A1 | 6/2019 | Halperin et al. |
| 2019/0254570 A1 | 8/2019 | Shinar et al. |
| 2019/0320987 A1 | 10/2019 | Halperin et al. |

FOREIGN PATENT DOCUMENTS

| | | |
|---|---|---|
| WO | 2007052108 A2 | 5/2007 |
| WO | 2008135985 A1 | 11/2008 |
| WO | 2009138976 A2 | 11/2009 |
| WO | 2012077113 A2 | 6/2012 |
| WO | 2013150523 A1 | 10/2013 |
| WO | 2015008285 A1 | 1/2015 |
| WO | 2016035073 A1 | 3/2016 |
| WO | 2020053719 A1 | 3/2020 |

\* cited by examiner

APPARATUS AND METHODS FOR MONITORING A SUBJECT

CROSS-REFERENCE TO RELATED APPLICATIONS

The present application is a continuation application of U.S. Ser. No. 16/877,543, published as US 2020/0275876 to Shinar, entitled "Apparatus and methods for monitoring a subject," filed May 19, 2020, which is a continuation of U.S. Ser. No. 15/431,842, published as US 2017/0231545, now abandoned, entitled "Apparatus and methods for monitoring a subject," filed Feb. 14, 2017, which claims the benefit of U.S. Provisional Application 62/295,077, entitled "Apparatus and method for monitoring a subject," filed Feb. 14, 2016.

The present application is related to International Patent Application PCT/IL2017/050182, published as WO 2017/138005, entitled "Apparatus and methods for monitoring a subject," filed Feb. 14, 2017.

Each of the above referenced applications is incorporated herein by reference.

FIELD OF EMBODIMENTS OF THE INVENTION

The present invention relates generally to monitoring a subject. Specifically, some applications of the present invention relate to monitoring a subject, while the subject is in a vehicle.

BACKGROUND

Quality and duration of sleep plays an important role in overall physical and psychological wellbeing. Unfortunately, many subjects have difficulty falling or staying asleep. Thermoregulation during sleep affects sleep quality.

An article entitled "Mechanisms and functions of coupling between sleep and temperature rhythms," by Van Someren (Prog Brain Res 2006, 153:309-324) describes heat production and heat loss as showing circadian modulation. The article states that sleep preferably occurs during the circadian phase of decreased heat production and increased heat loss, the latter due to a profound increase in skin blood flow and, consequently, skin warming.

An article entitled "Functional link between distal vasodilation and sleep-onset latency," by Kräuchi et al. (Am J Physiol Regul Integr Comp Physiol 2000, 278:R741-R748) describes a study in which the role of heat loss in sleep initiation was evaluated. The article states that the study provides evidence that selective vasodilation of distal skin regions (and hence heat loss) promotes the rapid onset of sleep.

An article entitled "Skin temperature and sleep-onset latency: Changes with age and insomnia," by Raymann et al. (Physiology & Behavior 90 (2007) 257-266) states that changes in skin temperature may causally affect the ability to initiate and maintain sleep. The article describes findings on the relation between skin temperature and sleep-onset latency, indicating that sleep propensity can be enhanced by warming the skin to the level that normally occurs prior to, and during, sleep. The article describes a study to investigate whether different methods of foot warming could provide an applicable strategy to address sleep complaints.

Summary of Embodiments

For some applications, a sensor unit is disposed under a seat of a vehicle. The sensor unit is configured to monitor physiological parameters of a subject who is sitting on the seat, and to generate a sensor signal in response thereto. Typically, the subject is an operator of the vehicle (e.g., the driver of a car, the pilot of an airplane, the driver of a train, etc.). A computer processor is configured to receive and analyze the sensor signal for any one of a number of reasons. Typically, the computer processor derives vital signs of the subject (such as heart rate, respiratory rate, and/or heart-rate variability) from the sensor signal. For some applications, the computer processor compares the subject's vital signs to a baseline of the subject that was derived during occasions when the subject previously operated the vehicle. In response thereto, the computer processor may determine that the subject's vital signs have changed substantially from the baseline, that the subject is unwell, drowsy, asleep, and/or under the influence of drugs or alcohol. In response thereto, the computer processor may generate an alert to the driver, or to a remote location (such as to a family member, and/or to a corporate control center). Alternatively or additionally, the computer processor may automatically disable the vehicle.

For some applications, the sensor unit is configured to be placed underneath the seat and to detect motion of the subject who is sitting on the seat during motion of the vehicle. The sensor unit typically includes a housing, at least one first motion sensor disposed within the housing, such that the first motion sensor generates a first sensor signal that is indicative of the motion of the vehicle, and at least one second motion sensor disposed within the housing, such that the second motion sensor generates a second sensor signal that is indicative of the motion of the subject and the motion of the vehicle. The computer processor is typically configured to at least partially distinguish between the motion of the subject and the motion of the vehicle by analyzing the first and second sensor signals.

For some applications of the present invention, a temperature control device (such as an electric blanket, or an electric mattress) includes at least first and second sections corresponding to respective portions of a body of a single subject. For example, a blanket may include three types of sections: a trunk section corresponding to the subject's trunk, leg sections corresponding to the subject's legs, and arm sections corresponding to the subject's arms. A temperature-regulation unit regulates respective portions of the subject's body to be at respective temperatures by, simultaneously, setting a temperature of the first section of the temperature control device to a first temperature, and setting a temperature of the second section of the temperature control device to a second temperature that is different from the first temperature. Optionally, the temperature-regulation unit sets the temperature of additional sections of the temperature control device to further respective temperatures.

As described hereinabove, thermoregulation during sleep affects sleep quality. Moreover, as described in the Kräuchi article for example, selective vasodilation of distal skin regions (and hence heat loss) may promote the onset of sleep. For some applications, a computer processor drives the temperature-regulation unit to regulate respective portions of the subject's body to be at respective temperatures in the manner described herein, such as to improve sleep quality, shorten sleep latency, and/or better maintain sleep continuity. For example, the computer processor may drive the temperature-regulation unit to regulate the temperature of the subject's legs and/or arms to be at a greater temperature than the subject's trunk (e.g., by heating the legs and/or arms by more than the trunk, or by cooling the trunk by less than the legs and/or arms). For some applications, the computer processor drives the temperature-regulation unit to regulate respective portions of the subject's body to be at respective temperatures, in response to the subject's sleep stage, which is detected automatically by analyzing a sensor signal from a sensor (such as motion sensor) that is configured to monitor the subject.

There is therefore provided, in accordance with some applications of the present invention, apparatus for use with a seat of a vehicle comprising:

a sensor unit configured to be placed underneath the seat and configured to detect motion of a subject who is sitting on the seat during motion of the vehicle, the sensor unit comprising:

a housing;

at least one first motion sensor disposed within the housing, such that the first motion sensor generates a first sensor signal that is indicative of the motion of the vehicle;

at least one second motion sensor disposed within the housing, such that the second motion sensor generates a second sensor signal that is indicative of the motion of the subject and the motion of the vehicle; and a computer processor configured to at least partially distinguish between the motion of the subject and the motion of the vehicle by analyzing the first and second sensor signals.

For some applications, the first motion sensor is disposed within the housing such that the first motion sensor is isolated from the motion of the subject, such that the first motion sensor only detects motion that is due to motion of the vehicle.

For some applications, the computer processor is configured to:

derive the motion of the vehicle from the first sensor signal, and based upon the derived motion of the vehicle, to subtract, from the second sensor signal, a portion of the second sensor signal that is generated by the motion of the vehicle.

For some applications:

at least a portion of the housing is flexible, the apparatus further comprises a fluid compartment disposed on an inner surface of the housing, the at least one first motion sensor is disposed on a surface of the fluid compartment, and at least one second motion sensor is disposed on at least one inner surface of the flexible portion of the housing.

For some applications, the first motion sensor comprises a sensor selected from the group consisting of: a deformation sensor, a piezoelectric sensor, and an accelerometer.

For some applications, the second motion sensor comprises a sensor selected from the group consisting of: a deformation sensor, a piezoelectric sensor, and an accelerometer.

For some applications, the at least one second motion sensor comprises two or more second motion sensors disposed on respective inner surfaces of the flexible portion of the housing.

For some applications:

the housing comprising flexible and rigid portions;

the at least one first motion sensor is disposed on at least one inner surface of the rigid portion of the housing;

the at least one second motion sensor is disposed on at least one inner surface of the flexible portion of the housing, and configured to generate a second sensor signal.

For some applications, the first motion sensor comprises a sensor selected from the group consisting of: a deformation sensor, a piezoelectric sensor, and an accelerometer.

For some applications, the second motion sensor comprises a sensor selected from the group consisting of: a deformation sensor, a piezoelectric sensor, and an accelerometer.

For some applications, the at least one first motion sensor comprises two or more first motion sensors disposed on respective inner surfaces of the rigid portion of the housing.

For some applications, the at least one second motion sensor comprises two or more second motion sensors disposed on respective inner surfaces of the flexible portion of the housing.

There is further provided, in accordance with some applications of the present invention, apparatus for use with a seat of a vehicle including:

a sensor unit configured to be placed underneath the seat and configured to detect motion of a subject who is sitting on the seat during motion of the vehicle, the sensor unit comprising:

a housing at least a portion of which is flexible;

a fluid compartment disposed on an inner surface of the housing;

at least one first motion sensor disposed on a surface of the fluid compartment, and configured to generate a first sensor signal;

at least one second motion sensor disposed on at least one inner surface of the flexible portion of the housing, the second motion sensor being configured to generate a second sensor signal; and a computer processor configured to at least partially distinguish between the motion of the subject and the motion of the vehicle by analyzing the first and second sensor signals.

In some applications, the first motion sensor includes a sensor selected from the group consisting of: a deformation sensor, a piezoelectric sensor, and an accelerometer.

In some applications, the second motion sensor includes a sensor selected from the group consisting of: a deformation sensor, a piezoelectric sensor, and an accelerometer.

In some applications, the at least one second motion sensor includes two or more second motion sensors disposed on respective inner surfaces of the flexible portion of the housing.

There is further provided, in accordance with some applications of the present invention, apparatus for use with a seat of a vehicle including:

a sensor unit configured to be placed underneath the seat and configured to detect motion of a subject who is sitting on the seat during motion of the vehicle, the sensor unit comprising:

a housing comprising flexible and rigid portions;

at least one first motion sensor disposed on at least one inner surface of the rigid portion of the housing, and configured to generate a first sensor signal;

at least one second motion sensor disposed on at least one inner surface of the flexible portion of the housing, and configured to generate a second sensor signal; and a computer processor configured to at least partially distinguish between the motion of the subject and the motion of the vehicle by analyzing the first and second sensor signals.

In some applications, the first motion sensor includes a sensor selected from the group consisting of: a deformation sensor, a piezoelectric sensor, and an accelerometer.

In some applications, the second motion sensor includes a sensor selected from the group consisting of: a deformation sensor, a piezoelectric sensor, and an accelerometer.

In some applications, the at least one first motion sensor includes two or more first motion sensors disposed on respective inner surfaces of the rigid portion of the housing.

In some applications, the at least one second motion sensor includes two or more second motion sensors disposed on respective inner surfaces of the flexible portion of the housing.

There is additionally provided, in accordance with some applications of the present invention, apparatus including:

a temperature-control device comprising at least first and second sections corresponding to respective portions of a body of a single subject; and a temperature-regulation unit configured to regulate temperatures of the respective portions of the subject's body to be at respective temperatures by, simultaneously, setting a temperature of the first section of the temperature-control device to a first temperature, and setting a temperature of the second section of the temperature control device to a second temperature that is different from the first temperature.

In some applications, the temperature control device includes a device selected from the group consisting of: a blanket and a mattress, and the selected device has a length of less than 250 cm, and a width of less than 130 cm.

In some applications, the temperature control device includes a blanket configured to be placed above the subject, and the first and second section include first and second sections that are configured to be placed over respective portions of the subject's body.

In some applications, the temperature control device includes a blanket configured to be disposed underneath the subject, and the first and second section include first and second sections that are configured to be disposed underneath respective portions of the subject's body.

In some applications, the temperature control device includes a mattress configured to be disposed underneath the subject, and the first and second section include first and second sections that are configured to be disposed underneath respective portions of the subject's body.

In some applications, the first section corresponds to a trunk of the subject, and the second section corresponds to a distal portion of the subject's body selected from the group consisting of: at least one arm of the subject, and at least one leg of the subject.

In some applications, the apparatus further includes:

a sensor, configured to monitor the subject and generate a sensor signal in response thereto; and a computer processor, configured to:

analyze the signal, in response thereto, identify a sleep stage of the subject, and in response to the identified sleep stage, drive the temperature-regulation unit to regulate the temperatures of the respective portions of the subject's body to be at the respective temperatures.

In some applications, the computer processor is configured to:

differentially identify at least two sleep stages selected from the group consisting of: a falling-asleep stage, a beginning-sleep stage, a mid-sleep stage, a premature-awakening stage, an awakening stage, a light sleep stage, a slow-wave sleep stage, and a rapid-eye-movement sleep stage, and in response to the differentially identified sleep stages, drive the temperature-regulation unit to regulate the temperatures of the respective portions of the subject's body to be at the respective temperatures.

In some applications, the sensor is configured to monitor the subject without contacting or viewing the subject, and without contacting or viewing clothes the subject is wearing.

In some applications, the first section corresponds to a trunk of the subject, and the second section corresponds to at least one distal portion of the subject's body selected from the group consisting of: at least one arm of the subject, and at least one leg of the subject.

In some applications, the computer processor is configured, in response to detecting that the subject is trying to fall asleep, to drive the temperature-modulation unit to regulate the subject's trunk to be at a first temperature, and to regulate at least the selected distal portion of the subject's body to be at a second temperature that is greater than the first temperature.

In some applications, the computer processor is configured, in response to detecting that the subject is at a sleep stage at which it is suitable to wake up the subject, to drive the temperature-regulation unit to heat the subject's trunk.

In some applications, the sensor includes a motion sensor configured to sense motion of the subject.

In some applications, the sensor is configured to monitor the subject without contacting or viewing the subject, and without contacting or viewing clothes the subject is wearing.

In some applications, the apparatus is for use with a room-climate regulation device, and, in response to the identified sleep stage, the computer processor is further configured to adjust a parameter of the room-climate regulation device.

In some applications, the room-climate regulation device includes an air-conditioning unit, and, in response to the identified sleep stage, the computer processor is configured to adjust a parameter of the air-conditioning unit.

There is further provided, in accordance with some applications of the present invention, apparatus for use with an output device, the apparatus including:

a sensor, configured to monitor a subject, during a sleeping session of the subject, and to generate a sensor signal in response to the monitoring; and a computer processor, configured to:

analyze the signal, in response thereto, identify a correspondence between positions of the subject and occurrences of apnea events of the subject during the sleeping session, and generate an output on the output device, in response to the identified correspondence.

There is further provided, in accordance with some applications of the present invention, apparatus for use with a female subject, the apparatus including:

a sensor, configured to monitor the subject, prior to the subject becoming pregnant and during a pregnancy of the subject, and to generate a sensor signal in response to the monitoring; and a computer processor, configured to:

analyze the sensor signal, based upon the sensor signal generated by the sensor in response to the monitoring prior to the subject becoming pregnant, to determine a baseline heart rate for the subject, based upon the baseline heart rate, define a pregnancy heart rate measure, which is indicative of one or more heart rates that the subject is expected to have during a healthy pregnancy, based upon the sensor signal generated by the sensor in response to the monitoring during the subject's pregnancy, determine a heart rate of the subject during the pregnancy, compare the subject's heart rate during the pregnancy to the pregnancy heart rate measure, and generate an output on the output device, in response to the comparison.

There is further provided, in accordance with some applications of the present invention, apparatus for use with a stimulus-providing device that is configured to provide a stimulus to a subject selected from the group consisting of: an audio stimulus, a visual stimulus, and a tactile stimulus, the apparatus including:

a sensor configured to monitor a subject and to generate a sensor signal in response thereto; and a control unit configured to:

analyze the sensor signal, modulate a property of the stimulus that is provided to the subject by the stimulus-providing device, in response to (a) the analyzing of the sensor signal, and (b) a historical physiological parameter of the subject that was exhibited in response to a historical modulation of the property of the stimulus, and drive the stimulus-providing device to provide the stimulus to the subject.

There is additionally provided, in accordance with some applications of the present invention, apparatus for monitoring a subject, the apparatus comprising:

a sensor, configured to monitor the subject without contacting the subject or clothes the subject is wearing, and without viewing the subject or clothes the subject is wearing, and to generate a sensor signal in response to the monitoring; and a computer processor, configured to:

receive the sensor signal, extract from the sensor signal a plurality of heartbeats of the subject, and, for each of the extracted heartbeats, an indication of a quality of the extracted heartbeat, select a subset of heartbeats, by selecting for inclusion in the subset only heartbeats for which qualities of both the heartbeat itself, and an adjacent heartbeat to the heartbeat, exceed a threshold, for only the subset of heartbeats, determining interbeat intervals between adjacent heartbeats, in response thereto, determining a physiological state of the subject, and generating an output in response thereto.

There is additionally provided, in accordance with some applications of the present invention, apparatus for monitoring a subject, the apparatus comprising:

a sensor, configured to monitor the subject and to generate a sensor signal in response thereto;

a plurality of filters configured to filter the sensor signal using respective filter parameters; and a computer processor, configured to:

receive the sensor signal, filter the signal with each of two or more of the filters, in response to a quality of each of the filtered signal, select one of the plurality of filters to filter the sensor signal, subsequently:

detecting that the subject has undergone motion, by analyzing the sensor signal, in response thereto, filtering the signal with each of two or more of the filters, and in response to a quality of each of the filtered signal, select one of the plurality of filters to filter the sensor signal.

The present invention will be more fully understood from the following detailed description of applications thereof, taken together with the drawings, in which:

DETAILED DESCRIPTION OF EMBODIMENTS

Figure 1:
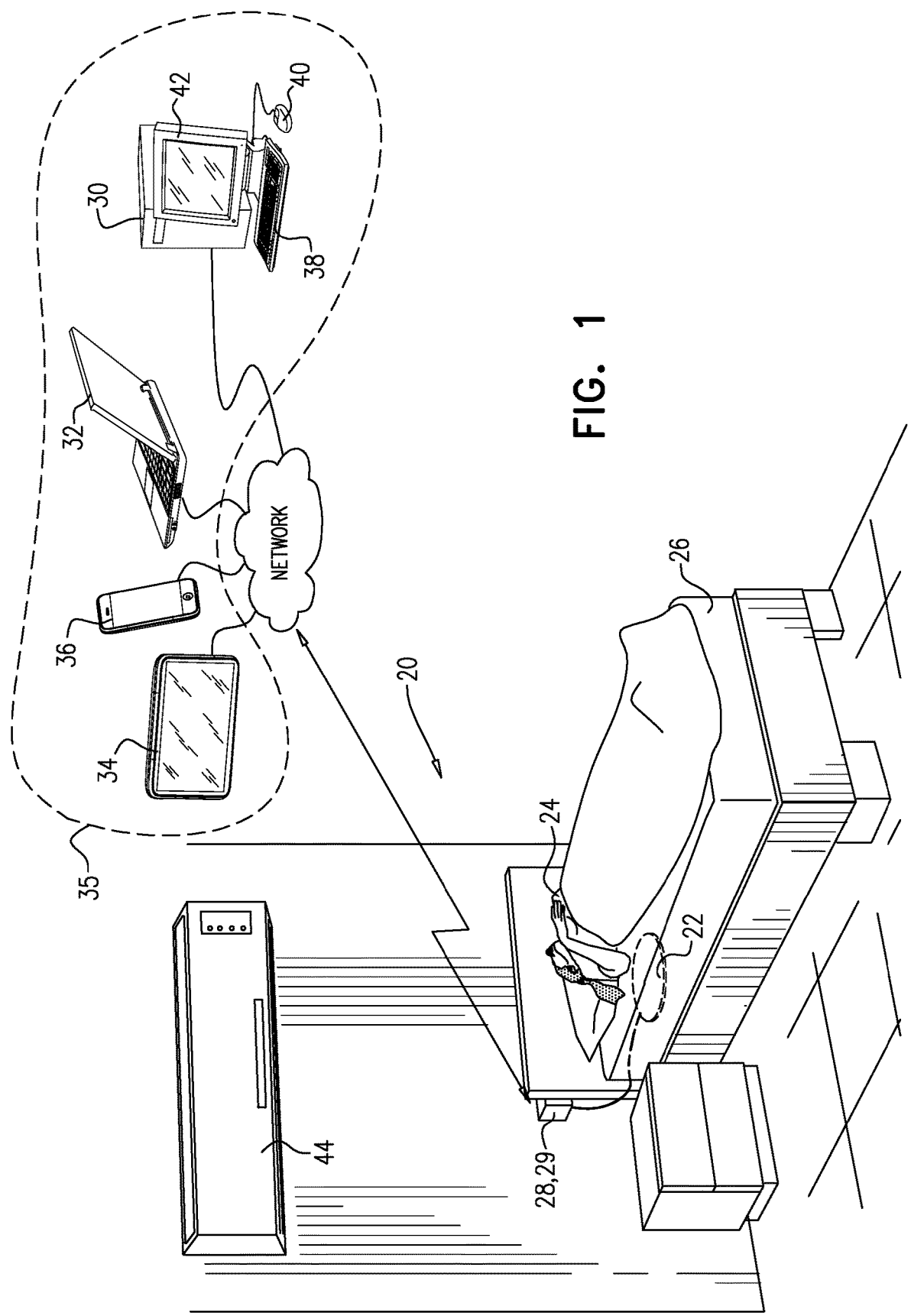
FIG. 1 is a schematic illustration of apparatus for monitoring a subject, in accordance with some applications of the present invention.

Reference is made to FIG. 1, which is a schematic illustration of subject-monitoring apparatus 20, in accordance with some applications of the present invention. Apparatus 20 is generally used to monitor a subject 24, while he or she is in his or her bed in a home setting. For some applications, the subject-monitoring apparatus is used in a hospital setting.

Subject-monitoring apparatus 20 comprises a sensor 22 (e.g., a motion sensor) that is configured to monitor subject 24. Sensor 22 may be a motion sensor that is similar to sensors described in U.S. Pat. No. 8,882,684 to Halperin, which is incorporated herein by reference. The term "motion sensor" refers to a sensor that senses the subject's motion (e.g., motion due to the subject's cardiac cycle, respiratory cycle, or large-body motion of the subject), while the term "sensor" refers more generally to any type of sensor, e.g., a sensor that includes an electromyographic sensor and/or an imaging sensor.

Typically, sensor 22 includes a sensor that performs monitoring of the subject without contacting the subject or clothes the subject is wearing, and/or without viewing the subject or clothes the subject is wearing. For example, the sensor may perform the monitoring without having a direct line of sight of the subject's body, or the clothes that the subject is wearing, and/or without any visual observation of the subject's body, or the clothes that the subject is wearing. Further typically, the sensor performs monitoring of the subject without requiring subject compliance (i.e., without the subject needing to perform an action to facilitate the monitoring that would not have otherwise been performed).

It is noted that, prior to the monitoring, certain actions (such as purchasing the sensor, placing the sensor under the subject's mattress, downloading software for use with the subject-monitoring apparatus, and/or configuring software for use with the subject-monitoring apparatus) may need to be performed. The term "without requiring subject compliance" should not be interpreted as excluding such actions. Rather the term "without requiring subject compliance" should be interpreted as meaning that, once the sensor has been purchased, placed in a suitable position and activated, the sensor can be used to monitor the subject (e.g., to monitor the subject during repeated monitoring sessions), without the subject needing to perform any actions to facilitate the monitoring that would not have otherwise been performed.

For some applications, sensor 22 is disposed on or within the subject's bed, and configured to monitor the subject automatically, while the subject is in their bed. For example, sensor 22 may be disposed underneath the subject's mattress 26, such that the subject is monitored while she is lying upon the mattress, and while carrying out her normal sleeping routine, without the subject needing to perform an action to facilitate the monitoring that would not have otherwise been performed.

A computer processor 28, which acts as a control unit that performs the algorithms described herein, analyzes the signal from sensor 22. Typically, computer processor 28 communicates with a memory 29. For some applications, computer processor 28 is embodied in a desktop computer 30, a laptop computer 32, a tablet device 34, a smartphone 36, and/or a similar device that is programmed to perform the techniques described herein (e.g., by downloading a dedicated application or program to the device), such that the computer processor acts as a special-purpose computer processor. For some applications, as shown in FIG. 1, computer processor 28 is a dedicated computer processor that receives (and optionally analyzes) data from sensor 22, and communicates with computer processors of one or more of the aforementioned devices, which act as external devices.

For some applications, the subject (or another person, such as a care-giver) communicates with (e.g., sends data to and/or receives data from) computer processor 28 via a user interface device 35. As described, for some applications, computer processor is embodied in a desktop computer 30, a laptop computer 32, a tablet device 34, a smartphone 36, and/or a similar device that is programmed to perform the techniques described herein. For such applications, components of the device (e.g., the touchscreen, the mouse, the keyboard, the speakers, the screen) typically act as user interface device 35. Alternatively, as shown in FIG. 1, computer processor 28 is a dedicated computer processor that receives (and optionally analyzes) data from sensor 22. For some such applications, the dedicated computer processor communicates with computer processors of one or more of the aforementioned external devices (e.g., via a network), and the user interfaces of the external devices (e.g., the touchscreen, the mouse, the keyboard, the speakers, the screen) are used by the subject, as user interface device 35, to communicate with the dedicated computer processor and vice versa. For some applications, in order to communicate with computer processor 28, the external devices are programmed to communicate with the dedicated computer processor (e.g., by downloading a dedicated application or program to the external device).

For some applications, user interface includes an input device such as a keyboard 38, a mouse 40, a joystick (not shown), a touchscreen device (such as smartphone 36 or tablet device 34), a touchpad (not shown), a trackball (not shown), a voice-command interface (not shown), and/or other types of user interfaces that are known in the art. For some applications, the user interface includes an output device such as a display (e.g., a monitor 42, a head-up display (not shown) and/or a head-mounted display (not shown)), and/or a different type of visual, text, graphics, tactile, audio, and/or video output device, e.g., speakers, headphones, smartphone 36, or tablet device 34. For some applications, the user interface acts as both an input device and an output device. For some applications, the processor generates an output on a computer-readable medium (e.g., a non-transitory computer-readable medium), such as a disk, or a portable USB drive.

Figure 2:
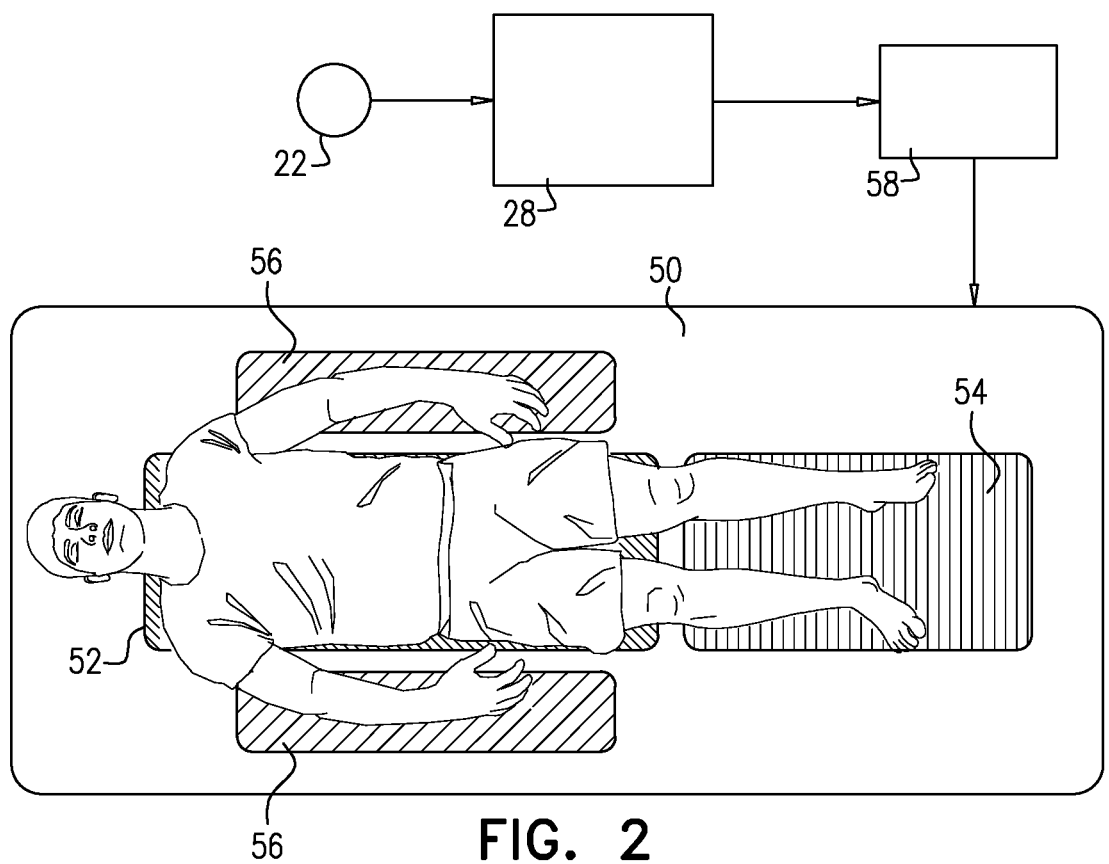
FIG. 2 is a schematic illustration of a blanket, in accordance with some applications of the present invention.

Reference is now made to FIG. 2, which is a schematic illustration of a temperature control device, e.g., a blanket 50 (which is typically an electric blanket), in accordance with some applications of the present invention. The temperature control device includes at least first and second sections corresponding to respective portions of a body of a single subject. For example, as shown the blanket includes three types of sections: a trunk section 52 corresponding to the subject's trunk, leg sections 54 corresponding to the subject's legs, and arm sections 56 corresponding to the subject's arms. A temperature-regulation unit 58 regulates respective portions of the subject's body to be at respective temperatures by, simultaneously, setting the temperature of the first section of the temperature control device to a first temperature, and setting the temperature of the second section of the temperature control device to a second temperature that is different from the first temperature, and, optionally, setting the temperatures of additional sections of the temperature control device to further respective temperatures.

It is noted that blanket 50 can be an over-blanket that is placed over the subject's body, or an under-blanket that is placed above the subject's mattress and beneath the subject (as shown). Furthermore, the scope of the present invention includes any temperature control device that includes first and second sections corresponding to respective portions of a body of a single subject, for use with a temperature-regulation unit that regulates the respective portions of the subject's body to be at respective temperatures by, simultaneously, setting the temperature of the first section of the temperature control device to a first temperature, and setting the temperature of the second section of the temperature control device to a second temperature that is different from the first temperature. For example, the temperature control device may include a mattress (e.g., an electric mattress), which includes built-in heating pads.

As described hereinabove, thermoregulation during sleep affects sleep quality. Moreover, as described in the Kräuchi article, for example, selective vasodilation of distal skin regions (and hence heat loss) may promote the onset of sleep. For some applications, the computer processor drives the temperature-regulation unit to regulate the temperatures of respective portions of the subject's body to be at respective temperatures, in the manner described herein, such as to improve sleep quality, shorten sleep latency, and/or better maintain sleep continuity. For example, the computer processor may drive the temperature-regulation unit to heat the subject's legs and/or arms to a greater temperature than the subject's trunk. For some applications, the computer processor may drive the temperature-regulation unit to cool one or more portions of the subject's body. For some applications, the computer processor drives the temperature-regulation unit to heat and/or cool respective portions of the subject's body to respective temperatures, in response to the subject's sleep stage, which is detected automatically by analyzing the sensor signal from sensor 22.

Figure 3:
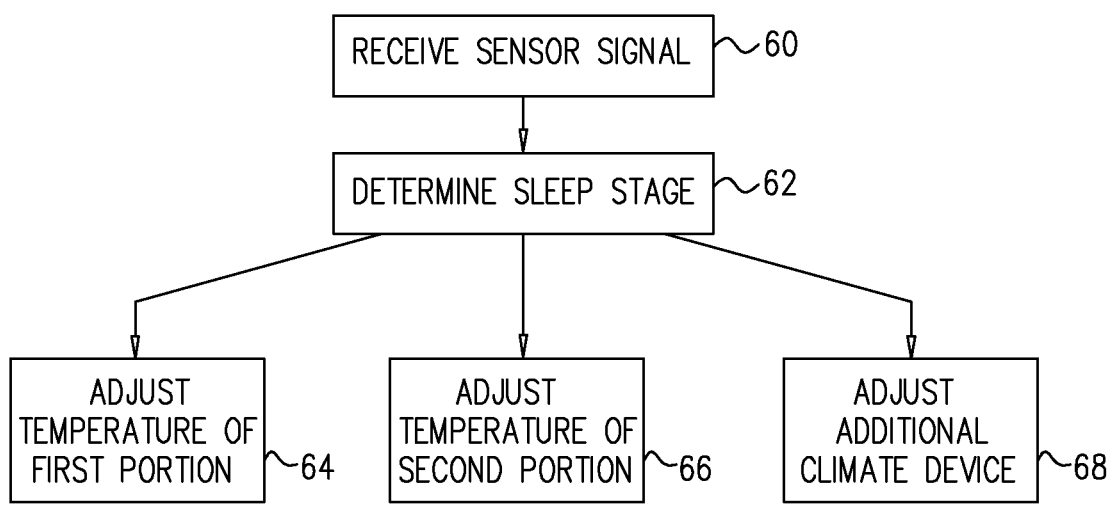
FIG. 3 is a flowchart showing steps that are performed by a computer processor in order to control a subject's body temperature, in accordance with some applications of the present invention.

Reference is now made to FIG. 3, which is a flowchart showing steps that are performed by a computer processor in order to control a subject's body temperature, in accordance with some applications of the present invention. In a first step 60, the computer processor receives a signal from sensor 22, which is typically as described hereinabove. In a second step 62, the computer processor analyzes the sensor signal in order to determine the subject's current sleep stage. For example, the computer processor may determine that the subject is currently in a falling-asleep stage (prior to falling asleep), a beginning-sleep stage, a mid-sleep stage, an awakening stage, a premature awakening stage, an REM stage, or a slow-wave stage. For some applications, the sleep stage is detected based upon the sensor signal using techniques as described in US 2007/0118054 to Pinhas (now abandoned), which is incorporated herein by reference. In response to the analysis of the sensor signal, the computer processor (in step 64) adjusts the temperature of a first portion of the temperature-control device (e.g., the arm or leg portion of blanket 50), and/or separately (in step 66) adjusts the temperature of a second portion of the temperature-control device (e.g., the trunk portion of blanket 50). For some applications (in step 68), the computer processor additionally adjusts the temperature of an additional room-climate regulation device, such as an air-conditioning unit (e.g., unit 44, FIG. 1), an electric heater, and/or a radiator. For example, the air-conditioning unit may be used to provide additional control of the temperature of the subject's trunk by controlling the temperature of the air that the subject inhales.

For some applications, in response to the computer processor determining that the subject is at the start of a sleeping session (e.g., in a falling-asleep stage or a beginning-sleep stage), the computer processor drives the temperature-regulation unit to heat distal parts of the subject's body (e.g., the subject's arms and/or legs) to a higher temperature than the subject's trunk. Typically, the computer processor will use different temperature profiles for different sleep states. For example, when the subject is in slow wave sleep, the computer processor may drive the temperature-regulation unit to keep temperatures lower than during other phases of the subject's sleep. Alternatively or additionally, when the subject wakes up during the night the computer processor may use a similar profile to that used when the subject is initially trying to fall asleep.

For some applications, the computer processor drives the temperature-regulation unit to warm the subject's trunk in order to gently wake up the subject. For example, the computer processor may use trunk warming to wake up the subject, based on having received an input of a desired time for the subject to wake up (e.g., via the user interface), or based on detecting that the current sleep phase of the subject is such that it would be a good time to wake up the subject.

For some applications, a user designates temperature profiles corresponding to respective sleep stages, via a user input into the computer processor. Typically, the temperature profile of any sleep stage will include respective temperatures for respective portions of the subject's body, and/or differences between the temperatures to which respective portions are heated or cooled. Alternatively or additionally, the computer processor utilizes a machine learning algorithm, based upon which the computer processor analyzes the subject's response to different temperature profiles at different sleep stages and learns which temperature profiles at which sleep phases result in the best quality sleep for the subject. Typically, for such applications, based upon the aforementioned analysis, the computer processor automatically designates temperature profiles to respective sleep stages.

As described hereinabove, for some applications, the computer processor additionally adjusts the temperature of an additional room-climate regulation device, such as an air-conditioning unit, an electric heater, and/or a radiator. For example, an air-conditioning unit may be used to provide additional control of the temperature of the subject's trunk by controlling the temperature of the air that the subject inhales. For some applications, the temperature profiles of the respective sleep stages include a setting for the additional room-climate regulation device.

Referring again to FIG. 2, it is noted that typically blanket is sized for use with a single subject, and includes separate regions the temperatures of which are controlled separately from one another. Typically, the length of the blanket is less than 250 cm, e.g., less than 220 cm, or less than 200 cm, and the width of the blanket is less than 130 cm, e.g., less than 120 cm, or less than 110 cm. For applications, in which the temperature-control device for use with a single subject is a mattress, typically, the mattress has similar dimensions to those described with respect to the blanket.

For some applications, the temperature control device is a portion of a blanket or a mattress that is suitable for being used by two subjects (e.g., partners in a double bed). Even for such applications, a portion of the blanket or mattress that is configured to be placed underneath or over a single subject (e.g., a left half of the blanket, or a left half of the mattress) includes at least first and second sections (e.g., a trunk section corresponding to the subject's trunk, leg sections corresponding to the subject's legs, and/or arm sections corresponding to the subject's arms), and the temperature-regulation unit regulates the respective portions of the subject's body to be at respective temperatures by, simultaneously, setting the temperature of the first section of the temperature control device to a first temperature, and setting the temperature the second section of the temperature control device to a second temperature that is different from the first temperature, and, optionally, setting the temperature of additional sections of the temperature control device to further respective temperatures.

Typically, the techniques described herein are practiced in combination with techniques described in WO 16/035073 to Shinar, which is incorporated herein by reference. For example, the computer processor may drive the user interface to prompt the subject to input changes to the temperature profiles corresponding to respective sleep stages, in response to a change in a relevant parameter. For example, in response to a change in season, an ambient temperature, an ambient humidity, and/or a going-to-sleep time (e.g., the subject is going to bed at an unusual time), the computer processor may drive the user interface to prompt the subject to re-enter his/her temperature profiles. (The computer processor may identify the change of the relevant parameter in a variety of ways, such as, for example, by receiving input from a sensor, or by checking the internet.)

For some applications, in response to analyzing the sensor signal, the computer processor calculates a sleep score of the subject. For example, the computer processor may calculate a score from one or more parameters such as a time to fall asleep, duration of sleep, or "sleep efficiency," which is the percentage of in-bed time during which the subject is sleeping. For some applications, the score is calculated using one or more of the aforementioned parameters, such that a higher sleep score is indicative of more restful sleeping session relative to a lower sleep score. The computer processor may then compare the sleep score to a baseline value, e.g., an average sleep score over a previous period of time. In response to the calculated sleep score being lower than the baseline value, the computer processor may drive the user interface to prompt the subject to re-enter new temperature profiles for respective sleep stages, since it is possible that the temperature profiles were a contributing factor in the subject's low sleep score. Alternatively or additionally, the computer processor may drive user interface to prompt the subject to input at least one factor that may have caused the low sleep score. The computer processor then controls the heating device in response to the input.

In some applications, the computer processor computes a measure of relaxation, i.e., a relaxation score, for the subject, one or more times during a sleeping session. For example, a high relaxation score may be computed if the subject shows little movement, and little variation in both respiration rate and respiration amplitude. The relaxation score may be used to compute the sleep score. Alternatively or additionally, in response to a low relaxation score, the computer processor may immediately adjust the temperature of sections of the temperature control device.

In some applications, in response to a low sleep score, the computer processor adjusts the temperature profiles even without any input from the user, or the computer processor generates an output (e.g., via user interface device 35) that includes suggested temperature profiles, which the subject may edit and/or confirm via the user interface.

For some applications, when the temperature control device is initially used by the subject, the computer processor is configured to perform a "sweep" (or "optimization routine") over a plurality of different temperature profiles at respective sleep stages, in order to ascertain which profiles at which sleep stages are conducive to a higher sleep score, relative to other settings, e.g., which setting maximizes the sleep score. For example, over the course of several sleeping sessions, the computer processor may change the temperature profiles that are used at respective sleep stages in different ways, and in response thereto, determine the optimal temperature profiles.

Additional techniques as described in WO 16/035073 to Shinar, which is incorporated herein by reference, may be practiced in combination with the apparatus and methods described herein.

Figure 4:
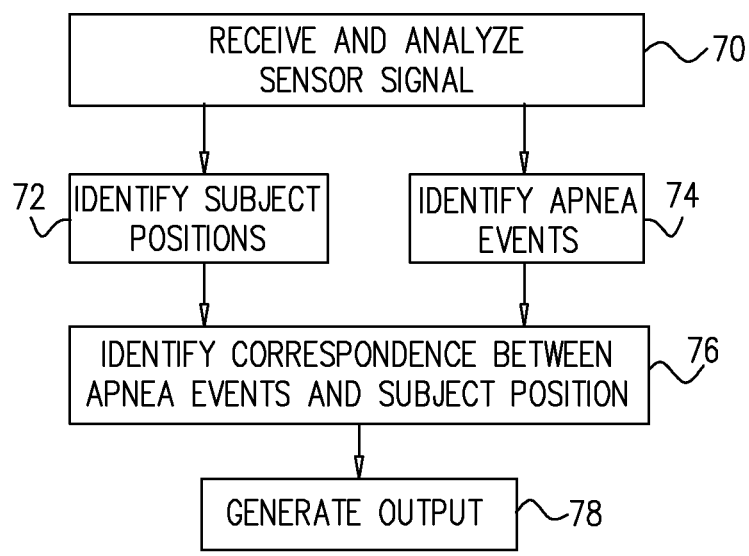
FIG. 4 is a flowchart showing steps that are performed by a computer processor in order to monitor sleep apnea of a subject, in accordance with some applications of the present invention.

Reference is now made to FIG. 4, which is a flowchart showing steps that are performed by computer processor 28 in order to monitor sleep apnea of the subject, in accordance with some applications of the present invention.

For some applications, sensor 22 is configured to monitor the subject during a sleeping session of the subject. The computer processor receives and analyzes the sensor signal (step 70). Based on the analysis of the signal, the computer processor identifies the positions of the subject's body at respective times during the sleeping session (step 72). For example, the system may identify when during the sleeping session the subject was lying on his/her side, when during the sleeping session the subject was lying on his/her back (i.e., supine), and when during the sleeping session the subject was lying on his/her stomach. For some applications, the computer processor determines the positions of the subject's body by analyzing the sensor signal using analysis techniques as described in U.S. Pat. No. 8,821,418 to Meger, which is incorporated herein by reference. For some applications, when the computer processor is first used for monitoring sleep apnea events, in accordance with the procedure shown in FIG. 4, a calibration process is performed by the processor. For example, the processor may instruct the subject to lie on his/her back, side, and stomach, each for a given time period. The processor analyzes the subject's cardiac and respiratory related waveforms, and/or other signal components of the sensor signal that are recorded when the subject is lying is respective positions. Based upon this analysis, the processor correlates respective signal characteristics to respective positions of the subject. Thereafter, the processor identifies the subject's position based upon characteristics of the sensor signal.

In addition, based upon the analysis of the sensor signal, the computer processor identifies apnea events that occur during the sleeping session (step 74). For example, the computer processor may identify apnea events by analyzing the sensor signal using analysis techniques as described in US 2007/0118054 to Pinhas (now abandoned), which is incorporated herein by reference. In step 76, the computer processor identifies a correspondence between positions of the subject and occurrences of apnea events of the subject during the sleeping session. The computer processor typically generates an output on an output device (e.g., any one of the output devices described with reference to FIG. 1), in response to the identified correspondence.

For example, the computer processor may generate an indication of:

(a) which positions cause the subject to undergo apnea events (e.g., "Sleeping on your back causes apnea events to occur"), (b) a recommended position for the subject to assume while sleeping (e.g. "Try sleeping on your side"), and/or (c) recommended steps to take in order to reduce the likelihood of apnea events occurring (e.g., "Try sleeping with a ball strapped to your back").

For some applications, the analysis of the sensor signal (step 70), the identification of subject positions (step 72), the identification of apnea events (step 74), and/or the identification of correspondence between the apnea events and the subject positions (step 76) are performed in real time, as the sensor signal is received by the processor. Alternatively, one or more of the aforementioned steps are performed subsequent to the sleeping session.

For some applications, in response to detecting that the subject is lying in a given position that the processor has determined to cause the subject to undergo apnea events, the computer processor generates an alert and/or nudges the subject to change positions. For example, in response to detecting that the subject is in a supine position (and having determined that lying in this position causes the subject to undergo apnea events), the computer processor may cause the subject's bed to vibrate, or may adjust the tilt angle of the bed or a portion thereof.

For some applications, techniques described herein are practiced in combination with techniques described in US 2007/0118054 to Pinhas, which is incorporated into the present application by reference. For example, the apparatus described herein may be used with a bed or mattress with an adjustable tilt angle, and/or an inflatable pillow which, when activated, inflates or deflates to vary the elevation of the head of the subject as desired. For some applications, in response to detecting that the subject is lying in a given position that the processor has determined to cause the subject to undergo apnea events, the pillow's air pressure level is changed, and/or the tilt angle of the bed or the mattress is changed, in order to change the patient's posture and prevent an upcoming apnea event, or stop a currently-occurring apnea event.

Typically, the techniques described herein are practiced in combination with techniques described in WO 16/035073 to Shinar, which is incorporated herein by reference. For some applications, a processor as described with reference to FIG. 4 is used in combination with a vibrating mechanism and/or an adjustable resting surface. The vibrating mechanism may include a vibrating mechanism disposed underneath mattress 26 and/or a vibrating wristwatch.

Typically, the subject is more likely to snore, cough, or have an apnea episode when the subject is in a supine position. The computer processor reduces the frequency of snoring, coughing, and/or apnea of subject 24 by encouraging (e.g., by "nudging") the subject to move from a supine position to a different position.

As described hereinabove the computer processor identifies the subject's sleeping position by analyzing the sensor signal from sensor 22. In response to the identified sleeping position, e.g., in response to the identified posture being a supine position, the computer processor drives the vibrating mechanism to vibrate, and/or adjusts a parameter (e.g., an angle) of the surface upon which the subject is lying. The vibration typically nudges the subject to change his posture, while the adjustment of the parameter may nudge the subject to change his posture or actually move the subject into the new posture.

In some applications, an inflatable pillow is used and the computer processor adjusts a level of inflation of the inflatable pillow. For example, to inhibit coughing and/or snoring, the computer processor may drive an inflating mechanism to inflate the inflatable pillow, by communicating a signal to the inflating mechanism.

As described hereinabove, for some applications, the computer processor is configured to identify a sleep stage of the subject. For some such applications, the computer processor drives the vibrating mechanism to vibrate, and/or adjusts the parameter of the resting surface, further in response to the identified sleep stage. For example, the computer processor may drive the vibrating mechanism to vibrate, and/or adjust the parameter of the resting surface, in response to the identified sleep stage being within 5 minutes of an onset or an end of an REM sleep stage, since at these points in time, the "nudging" or moving is less likely to disturb the subject's sleep.

Figure 5:
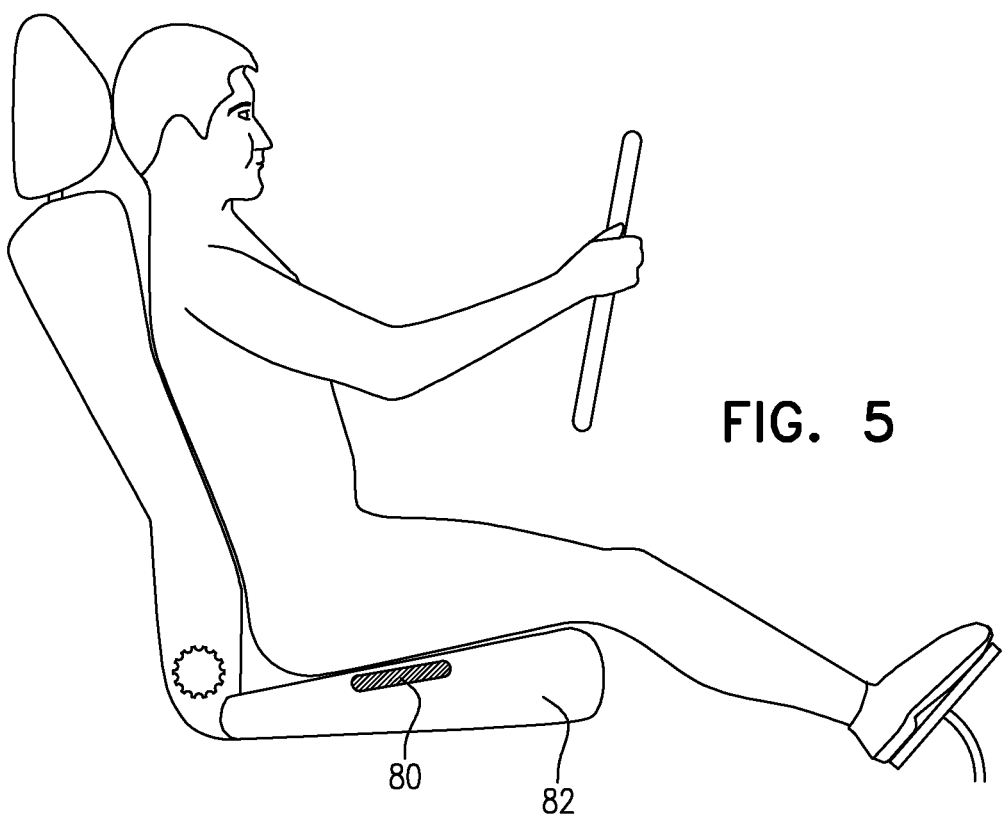
FIG. 5 is a schematic illustration of a sensor unit disposed under the seat of a vehicle, in accordance with some applications of the present invention.

Reference is now made to FIG. 5 is a schematic illustration of a sensor unit 80 disposed under a seat 82 of a vehicle, in accordance with some applications of the present invention. Sensor unit 80 is configured to monitor physiological parameters of a subject who is sitting on seat 82, and to generate a sensor signal in response thereto. Typically, the subject is an operator of the vehicle (e.g., the driver of a car, the pilot of an airplane, the driver of a train, etc.). A computer processor, which is typically like computer processor 28 described herein, is configured to receive and analyze the sensor signal for any one of a number of reasons.

Typically, the computer processor derives vital signs of the subject (such as heart rate, respiratory rate, and/or heart-rate variability) from the sensor signal. For some applications, the computer processor compares the subject's vital signs to a baseline of the subject that was derived during previous occasions when the subject operated the vehicle. In response thereto, the computer processor may determine that the subject's vital signs have changed substantially from the baseline, that the subject is unwell, drowsy, asleep, and/or under the influence of drugs or alcohol. In response thereto, the computer processor may generate an alert to the driver, or to a remote location (such as to a family member, and/or to a corporate control center). Alternatively or additionally, the computer processor may automatically disable the vehicle.

For some applications, the computer processor integrates the analysis of the sensor signal from sensor unit 80 with the analysis of a sensor signal from an additional sensor, which may be disposed in the subject's bed, for example. For example, the computer processor may determine that the subject has not had enough sleep based upon the analysis of the signals from both sensors. Or, the sensor may derive, from the combination of the sensor signals, that the subject has had enough sleep, but appears to be unwell, and/or under the influence of drugs or alcohol. In response thereto, the computer processor may generate an alert to the driver, or to a remote location (such as to a family member, and/or to a corporate control center). Alternatively or additionally, the computer processor may automatically disable the vehicle.

For some applications, sensor units 80 are disposed underneath more than one seat in the vehicle. For example, sensor units may be disposed underneath the seats of a pilot and a co-pilot in an airplane (e.g., as described in WO 16/035073 to Shinar, which is incorporated herein by reference). Or, sensor units may be disposed underneath each of the seats in an airplane or a car. Based upon the sensor signals from the sensor units, the computer processor may determine that a child has been left alone in a car, and may generate an alert in response thereto. For example, the alert may be generated on the driver's and/or parents' cellular phone(s). Alternatively or additionally, the computer processor may determine the number of people in the car. (It is noted that the sensor is typically configured to distinguish between a person who is disposed upon the seat and an inanimate object (such as a suitcase, or backpack) that is disposed upon the seat.) In response thereto, the computer processor may generate seatbelt alerts, for example. Alternatively or additionally, the computer processor may automatically communicate with the billing system of a toll road for which prices are determined based upon the number of passengers in the car.

Typically, in order to facilitate the above-described applications, sensor unit 80 is configured to generate a sensor signal that is such that the computer processor is able to distinguish between artifacts from motion of vehicle, and motion that is indicative of physiological parameters of the subject. Typically, the sensor unit includes (a) a housing, (b) at least one first motion sensor disposed within the housing, such that the first motion sensor generates a first sensor signal that is indicative of the motion of the vehicle, and (c) at least one second motion sensor disposed within the housing, such that the second motion sensor generates a second sensor signal that is indicative of the motion of the subject and the motion of the vehicle. The computer processor configured to at least partially distinguish between the motion of the subject and the motion of the vehicle by analyzing the first and second sensor signals.

For some applications, the first motion sensor is disposed within the housing, such that the first motion sensor is isolated from the motion of the subject, and/or such that the first motion sensor only detects motion that is due to motion of the vehicle. The computer processor at least partially distinguishes between the motion of the subject and the motion of the vehicle by (a) deriving the motion of the vehicle from the first sensor signal(s), and (b) based upon the derived motion of the vehicle, subtracting the vehicular motion (i.e., subtracting the portion of the sensor signal that is generated by the motion of the vehicle) from the sensor signal that is generated by the second sensor(s).

Figure 6A:
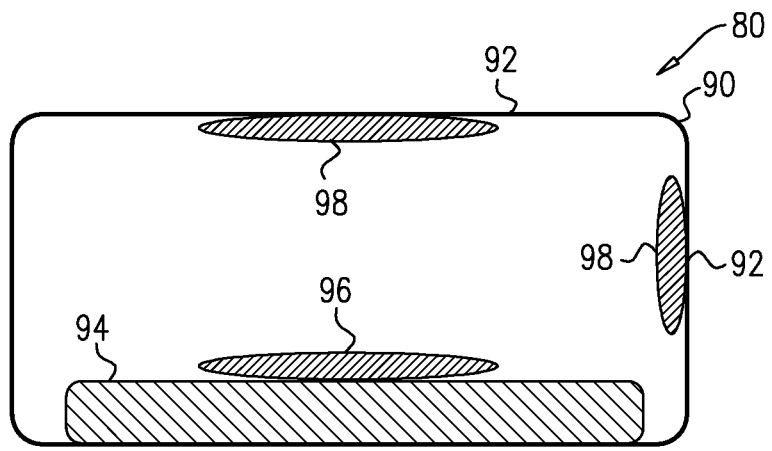
FIGS. 6A-C are schematic illustrations of a sensor unit as shown in FIG. 5, in accordance with respective applications of the present invention.
Figure 6B:
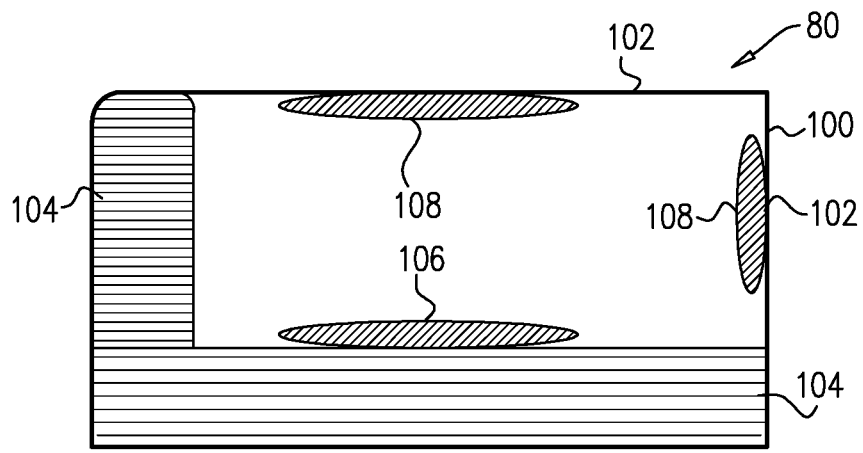
Figure 6C:
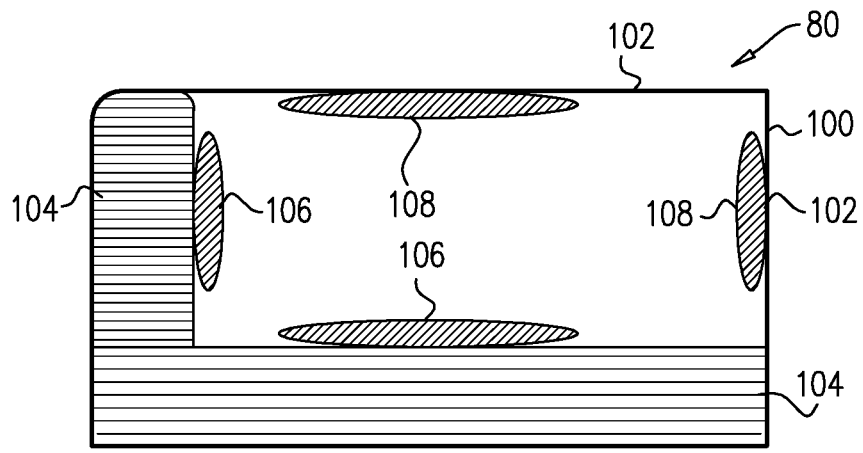

Reference is now made to FIGS. 6A-C are schematic illustrations of sensor unit 80, in accordance with respective applications of the present invention.

As shown in FIG. 6A, for some applications, sensor unit 80 includes a housing 90 at least a portion 92 of which is flexible. A fluid compartment 94, which is filled with a gas or a liquid, is disposed on an inner surface of the housing. A first motion sensor 96 (e.g., a deformation sensor, a piezoelectric sensor, and/or an accelerometer) is disposed on a surface of the fluid compartment, and is configured to generate a first sensor signal. For some applications (not shown), two or more first motion sensors are disposed on the surface of the fluid compartment, and each of the first motion sensors generates a respective sensor signal. A second motion sensor 98 (e.g., a deformation sensor, a piezoelectric sensor, and/or an accelerometer) is disposed on at least one inner surface of flexible portion 92 of housing 90. The second motion sensor is configured to generate a second sensor signal. For some applications, as shown, two or more motion sensors 98 are disposed on respective inner surfaces of flexible portion 92 of housing 90, and each of motion sensors 98 generates a respective sensor signal. The computer processor is configured to at least partially distinguish between the motion of the subject and the motion of the vehicle by analyzing the first and second sensor signals.

Typically, fluid compartment 94 isolates first motion sensor 96 from motion of the subject who is sitting on the seat, such that motion sensor 96 only detects motion that is due to motion of the vehicle. Second motion sensor(s) detects both motion of the vehicle, and motion of the subject, the motion of the subject being conveyed to the second motion sensor(s) via the flexible portion of the housing. Thus, the computer processor at least partially distinguishes between the motion of the subject and the motion of the vehicle by (a) deriving the motion of the vehicle from the first sensor signal, and (b) based upon the derived motion of the vehicle, subtracting the vehicular motion (i.e., subtracting the portion of the sensor signal that is generated by the motion of the vehicle) from the sensor signal that is generated by the second sensor(s).

As shown in FIGS. 6B and 6C, for some applications, sensor unit 80 includes a housing 100 that includes a flexible portion 102 and a rigid portion 104. At least one first motion sensor(s) 106 (e.g., a deformation sensor, a piezoelectric sensor, and/or an accelerometer) is disposed on at least one inner surface of the rigid portion of the housing, and is configured to generate a first sensor signal. For some applications, as shown in FIG. 6C, two or more first motion sensors are disposed on respective inner surfaces of the rigid portion of the housing, and each of motion sensors 106 generates a respective sensor signal. At least one second motion sensor 108 (e.g., a deformation sensor, a piezoelectric sensor, and/or an accelerometer) is disposed on at least one inner surface of flexible portion 102 of housing 100. The second motion sensor is configured to generate a second sensor signal. For some applications, as shown in FIGS. 6B and 6C, two or more motion sensors 108 are disposed on respective inner surfaces of flexible portion 102 of housing 100, and each of motion sensors 108 generates a respective sensor signal. The computer processor is configured to at least partially distinguish between the motion of the subject and the motion of the vehicle by analyzing the first and second sensor signals.

Typically, the rigidity of the rigid portion of the housing isolates first motion sensor(s) 106 from motion of the subject who is sitting on the seat, such that first motion sensor(s) 106 only detects motion that is due to motion of the vehicle. Second motion sensor(s) detects both motion of the vehicle, and motion of the subject, the motion of the subject being conveyed to the second motion sensor(s) via the flexible portion of the housing. Thus, the computer processor at least partially distinguishes between the motion of the subject and the motion of the vehicle by (a) deriving the motion of the vehicle from the first sensor signal(s), and (b) based upon the derived motion of the vehicle, subtracting the vehicular motion (i.e., subtracting the portion of the sensor signal that is generated by the motion of the vehicle) from the sensor signal that is generated by the second sensor(s).

Typically, the techniques described herein are practiced in combination with techniques described in WO 16/035073 to Shinar, which is incorporated herein by reference. For some applications, a sensor unit as described with reference to FIGS. 5-6C is used in an airplane, and the computer processor generates one or more of the following outputs, based upon analysis of the sensor signal:

(a) An alert may be generated if, by analyzing the sensor signal, the computer processor identifies an elevated stress level of a subject, e.g., by identifying an elevated heart rate, and/or a decreased stroke volume, e.g., as described in WO 2015/008285 to Shinar, which is incorporated herein by reference. For example, in response to the pilot experiencing an elevated stress level, the computer processor may generate an alert to another member of the flight crew, and/or individuals on the ground. The computer processor may also analyze the signal of the co-pilot, and generate an alert in response to both the pilot and co-pilot experiencing an elevated stress level, since the presence of an elevated stress level in both individuals at the same time is likely to be indicative of an emergency situation. Similarly, an alert may be generated if two or more passengers experience an elevated stress level at the same time.

(b) An alert may be generated if, by analyzing the sensor signal, the computer processor identifies that it is likely that the subject is experiencing, or will soon experience, a clinical event, such as a heart attack. For example, if the pilot or one of the passengers is experiencing a heart attack, members of the flight crew, and/or a physician who is travelling on the airplane, may be alerted to the situation.

(c) An alert may be generated if, by analyzing the sensor signal, the computer processor identifies that it is at least somewhat likely that the subject is a carrier of a disease, such as severe acute respiratory syndrome (SARS). For example, if the computer processor identifies a change in the baseline heart rate of the subject without any correlation to motion of the subject, the computer processor may ascertain that the subject has likely experienced a rapid change in body temperature, which may indicate that the subject is sick. (The baseline heart rate is typically an average heart rate over a period of time, e.g., 1-2 hours.) In response, the computer processor may alert the flight crew to isolate the subject.

(d) An alert may be generated if, by analyzing the sensor signal, the computer processor identifies that the subject (in particular, the pilot or co-pilot) is drowsy or sleeping.

(e) A sleep study may be performed. For example, the computer processor may analyze the sensor signals from various passengers, and identify which passengers were sleeping at which times. In response, the computer processor may generate an output to help the airline improve the sleeping conditions on their aircraft (e.g., by reducing lighting, or increasing leg room).

The computer processor may also control the lighting, temperature, or other cabin-environment parameters, in order to facilitate a more pleasant travelling experience. For example, upon detecting that a significant number of passengers are sleeping or are trying to fall asleep, the lights in the cabin may be dimmed, and/or the movie that is playing may be stopped. Alternatively or additionally, meals may be served to the passengers only if a given number of passengers are awake. To help prevent deep vein thrombosis (DVT), passengers may be prompted to stand up and take a walk, if the computer processor detects that they have been sitting in place for too long.

Figure 7A:
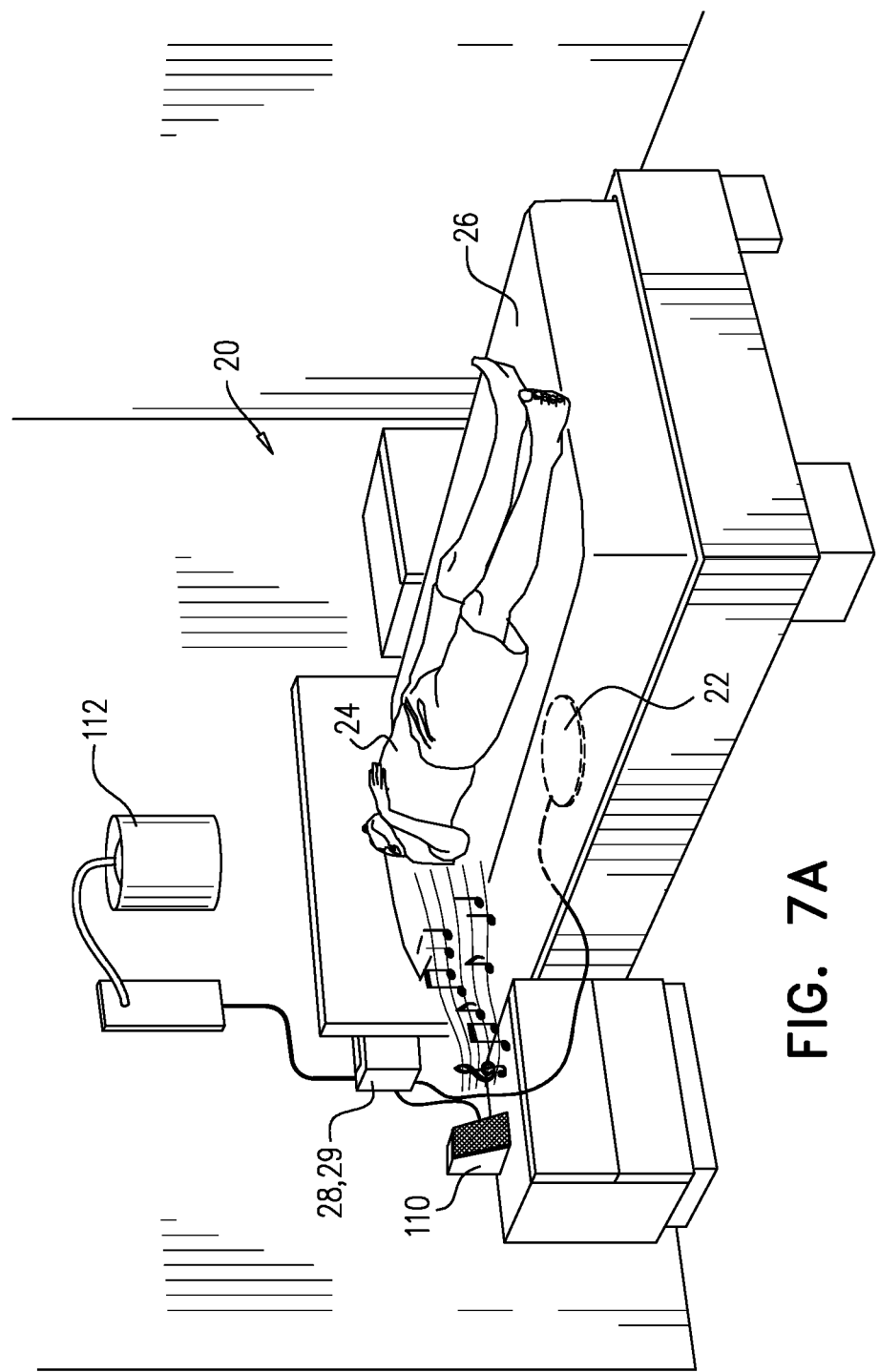
FIGS. 7A-B are schematic illustrations of subject-monitoring apparatus, in accordance with some applications of the present invention.
Figure 7B:
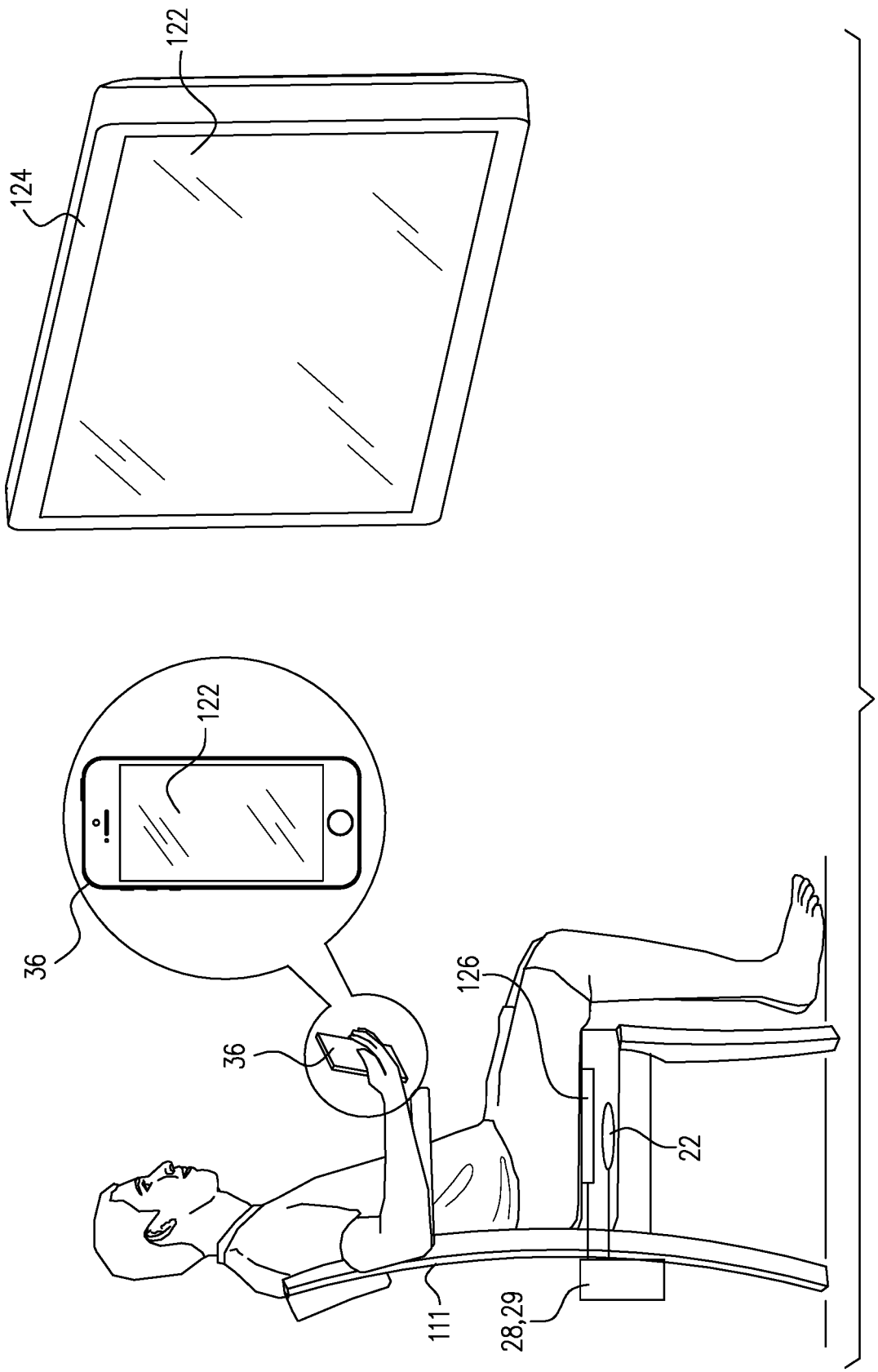

Reference is now made to FIGS. 7A-B, which are schematic illustrations of subject-monitoring apparatus, in accordance with some applications of the present invention. Components of subject-monitoring apparatus 20 are as described hereinabove with reference to FIG. 1. For some applications, as shown in FIG. 7B sensor 22 is disposed under a chair 111 that the subject sits upon, and is configured to monitor the subject while the subject is sitting on the chair, in the manner described hereinabove, mutatis mutandis. For some applications techniques described herein are practiced in combination with techniques described in WO 16/035073 to Shinar, which is incorporated herein by reference.

Subject-monitoring apparatus 20 comprises a sensor 22, which is generally as described hereinabove, and is configured to monitor subject 24. Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22. It is noted that, in general, in the specification and claims of the present application, the terms "computer processor" and "control unit" are used interchangeably, since steps of the techniques described herein are typically performed by a computer processor that functions as a control unit. Therefore, the present application refers to component 28 both as a "computer processor" and a "control unit."

In response to the analyzing the signal from sensor 22, computer processor 28 controls a property (e.g., the content, genre, volume, frequency, and/or phase-shift) of a sound signal, and drives a speaker 110 to play the sound signal. Typically, as described hereinbelow, the property of the sound signal is controlled such as to help the subject fall asleep or remain asleep.

For example, if the subject is trying to fall asleep, the computer processor may select a sound signal of the "relaxing nature sounds" genre, and may further select the content of the signal to be the sound of waves hitting the seashore. The computer processor may further set the frequency of the sound signal (e.g., the frequency of the waves) to an offset less than the subject's current heart rate or respiratory rate, in order to facilitate slowing of the subject's heart rate and/or respiratory rate. In some applications, the computer processor controls the offset, in response to analyzing the sensor signal; for example, as the heart rate of the subject approaches a target "relaxed" heart rate, the computer processor may reduce the offset, such that the frequency of the sound signal is very close to or identical with the subject's heart rate. As the subject begins to fall asleep, the computer processor may reduce the volume of the sound signal.

In some applications, the computer processor controls a phase-shift of the sound signal with respect to a cardiac signal and/or a respiratory signal of the subject. For example, the computer processor may cause the sound of a wave hitting the seashore to occur a given amount of time (e.g., 300 milliseconds) before or after each heartbeat of the subject, or a given amount of time (e.g., 1 second) after each expiration of the subject.

In some applications, the computer processor ascertains that the subject is trying to fall asleep, at least in response to analyzing the sensor signal. For example, by analyzing the sensor signal, the computer processor may ascertain that the subject is awake and is exhibiting a large amount of movement indicative of restlessness in bed. Alternatively or additionally, the ascertaining is in response to one or more other factors, such as a signal from a light sensor that indicates a low level of ambient light in the room, and/or the time of day. In response to ascertaining that the subject is trying to fall asleep, the computer processor controls the property of the sound signal, as described hereinabove.

In some applications, by analyzing the sensor signal, the computer processor ascertains a sleep stage of the subject, and controls the property of the sound signal in response to the ascertained sleep stage. For example, in response to ascertaining that the subject has entered a slow-wave (i.e., deep) sleep stage, the volume of the sound signal may be reduced to a relatively low level (e.g., zero). (In identifying a sleep stage of a subject, as described throughout the present application, the computer processor may use one or more of the techniques described in (a) US 2007/0118054 to Pinhas (now abandoned), and/or (b) Shinar et al., Computers in Cardiology 2001; Vol. 28: 593-596, and (c) Shinar Z et al., "Identification of arousals using heart rate beat-to-beat variability," Sleep 21(3 Suppl):294 (1998), each of which is incorporated herein by reference.)

Typically, the computer processor controls the property of the sound signal further in response to a historical physiological parameter of the subject that was exhibited in response to a historical sound signal. For example, the computer processor may "learn" the subject's typical responses to particular sound-signal properties, and control the sound signal in response thereto. Thus, for example, if the subject has historically responded well to a "relaxing nature sounds" genre, but less so to a "classical music" genre, the computer processor may select the former genre for the subject. To determine whether the subject has historically responded well to particular properties of the sound signal, the computer processor looks at some or all of historical physiological parameters such as a quality of sleep, a time-to-fall-asleep, a heart-rate-variability, a change in heart rate, a change in respiratory rate, a change in heart-rate-variability, a change in blood pressure, a rate of change in heart rate, a rate of change in respiratory rate, a rate of change in heart-rate-variability, and a rate of change in blood pressure.

In some applications, the computer processor controls the frequency of the sound signal by synthesizing the sound signal, or by selecting a pre-recorded sound signal that has the desired frequency; in other words, the computer processor selects the content of the signal, without the user's input. In other applications, the computer processor selects content of the sound signal in response to a manual input, e.g., an input entered via user interface device 35 (FIG. 1). For example, the subject may select a particular piece of classical music, and the computer processor may then control properties (such as the frequency, i.e., the tempo) of that particular piece. This may be done, for example, using appropriate software, such as Transcribe!™ by Seventh String Software of London, UK.

For some applications, in response to parameters of the signal detected by sensor 22, the computer processor controls a property of light (such as intensity, flicker frequency, or color) emitted by a light 112 in a generally similar manner to that described with respect to controlling the sound that is generated by speaker 110, mutatis mutandis. For example, the computer processor may select a light signal that causes the subject to enter a relaxed state, in response to detecting that the subject is trying to fall asleep. Alternatively or additionally, the computer processor may modulate the property of the light at a frequency of modulation that is based upon the subject's current heart rate or respiratory rate, in order to facilitate slowing of the subject's heart rate and/or respiratory rate, as described hereinabove with respect to the sound signal. Further alternatively or additionally, the computer processor may ascertain a sleep stage of the subject, and modulate the property of the light in response to the ascertained sleep stage. For some applications, the computer processor controls the property of the light further in response to a historical physiological parameter of the subject that was exhibited in response to a historical light signal. For example, the computer processor may "learn" the subject's typical responses to particular light-signal properties, and control the light in response thereto. The computer processor may control parameters of light 112, as an alternative to, or in addition to, controlling properties of the sound that is generated by speaker 110.

For some applications, in response to parameters of the signal detected by sensor 22, the computer processor controls a property of light (such as intensity, flicker frequency, or color) that is emitted by a screen 122 of a device that the subject is using in a generally similar manner to that described with respect to controlling the sound that is generated by speaker 110, mutatis mutandis. For example, the device may be a laptop computer 32 (FIG. 1), a tablet device 34 (FIG. 1), a smartphone 36 (FIG. 7B), and or a TV 124 (FIG. 7B). For example, the computer processor may select a light signal that causes the subject to enter a relaxed state, in response to detecting that the subject is trying to fall asleep. Alternatively or additionally, the computer processor may modulate the property of the light at a frequency of modulation that is based upon the subject's current heart rate or respiratory rate, in order to facilitate slowing of the subject's heart rate and/or respiratory rate, as described hereinabove with respect to the sound signal. Further alternatively or additionally, the computer processor may ascertain a sleep stage of the subject, and modulate the property of the light in response to the ascertained sleep stage. For some applications, the computer processor controls the property of the light further in response to a historical physiological parameter of the subject that was exhibited in response to a historical light signal. For example, the computer processor may "learn" the subject's typical responses to particular light-signal properties, and control the light in response thereto. The computer processor may control parameters of light emitted by screen 122, as an alternative to, or in addition to, controlling parameters of the sound that is generated by speaker 110, and/or light that is generated by light 112.

For some applications, a vibrating element 126 is disposed underneath a surface of chair 111 upon which the subject sits. Alternatively (not shown), a vibrating element may be disposed underneath the surface of the bed upon which the subject lies. For some applications, in response to parameters of the signal detected by sensor 22, the computer processor controls a property of the vibration (such as vibrating frequency, or a strength of vibration) that is applied to the subject by the vibrating element, in a generally similar manner to that described with respect to controlling the sound that is generated by speaker 110, mutatis mutandis. For example, the computer processor may select a vibration signal that causes the subject to enter a relaxed state, in response to detecting that the subject is trying to fall asleep. Alternatively or additionally, the computer processor may modulate the property of the vibration at a frequency of modulation that is based upon the subject's current heart rate or respiratory rate, in order to facilitate slowing of the subject's heart rate and/or respiratory rate, as described hereinabove with respect to the sound signal. Further alternatively or additionally, the computer processor may ascertain a sleep stage of the subject, and modulate the property of the vibration in response to the ascertained sleep stage. For some applications, the computer processor controls the property of the vibration further in response to a historical physiological parameter of the subject that was exhibited in response to a historical vibration signal. For example, the computer processor may "learn" the subject's typical responses to particular vibration-signal properties, and control the vibrating element in response thereto. The computer processor may control parameters of the vibration of the vibrating element, as an alternative to, or in addition to, controlling parameters of the sound that is generated by speaker 110, and/or light that is generated by light 112 or by screen 122.

It is noted that, typically, for any of the embodiments described with reference to FIGS. 7A-B, in response to analysis of the signal from sensor 22, computer processor controls a property of a stimulus-providing device, in a manner that changes a physiological parameter of the subject, such as the subject's heart rate, respiration rate, or sleep latency period. The stimulus-providing device may provide an audio stimulus (e.g., speaker 110), a visual stimulus (e.g., light 112 or screen 122), or a tactile stimulus (e.g., vibrating element 126). Typically, the stimulus is provided to the subject in a manner that does not require any compliance by the user, during the provision of the stimulus to the subject. (Prior to the monitoring of the subject and providing the stimulus to the subject, certain actions (such as purchasing the sensor, placing the sensor under the subject's mattress or chair, downloading software for use with the subject-monitoring apparatus, configuring software for use with the subject-monitoring apparatus, or turning on the stimulus providing device) may need to be performed. The term "without requiring subject compliance" should not be interpreted as excluding such actions.) Typically, the subject may perform routine activities (such as browsing the internet, or watching TV), and while the subject is performing routine activities, the computer processor automatically controls a property of the stimulus that is provided to the subject in the above-described manner. Furthermore, typically the stimulus is provided to the subject in manner that does not require the subject to consciously change the physiological parameter upon which the stimulus has an effect. Rather, the stimulus is provided to the subject such that the physiological parameter of the subject is changed without requiring the subject to consciously adjust the physiological parameter.

Figure 8:
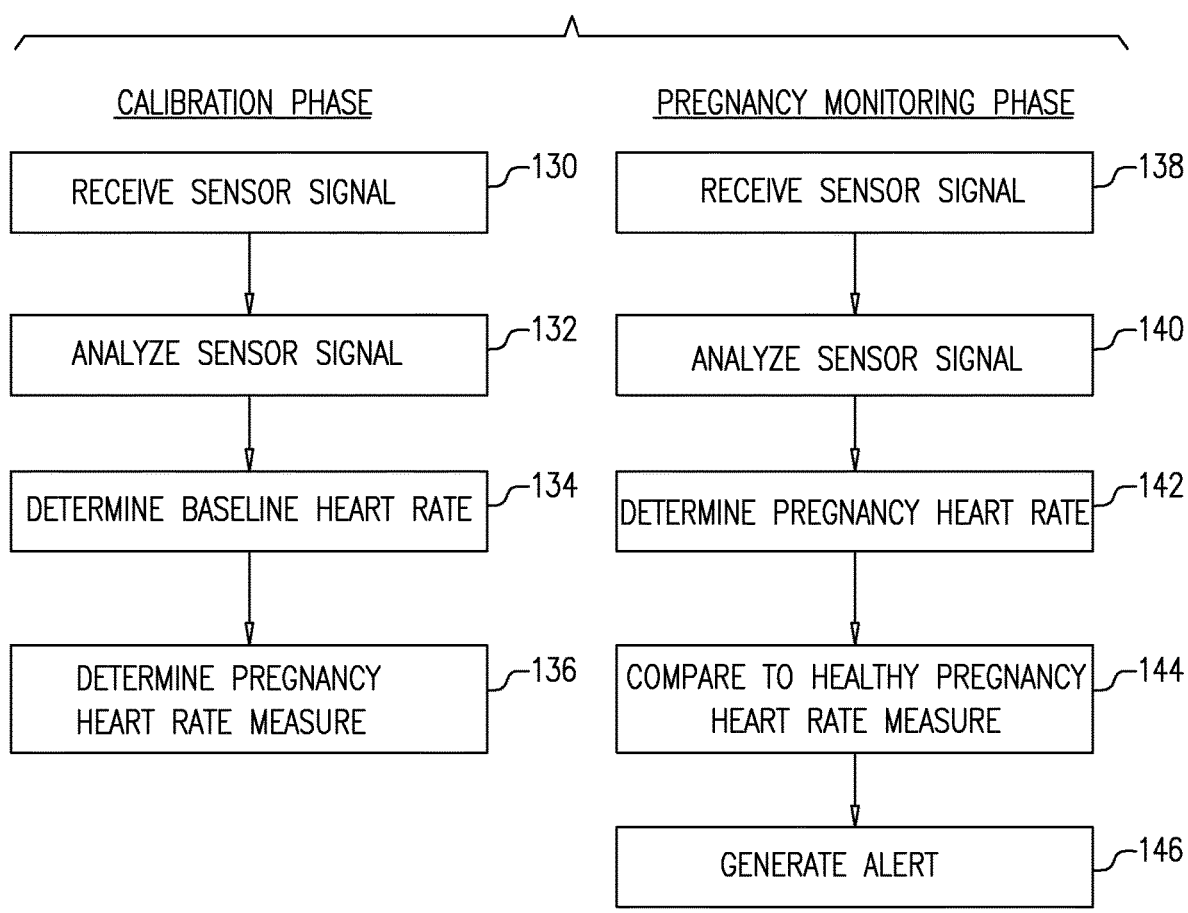
FIG. 8 is a flowchart showing steps that are performed by a computer processor in order to monitor a subject who is pregnant, in accordance with some applications of the present invention.

FIG. 8 is a flowchart showing steps that are performed by a computer processor in order to monitor a subject who is pregnant, in accordance with some applications of the present invention. A pregnant woman's heart rate is typically expected to increase during pregnancy and be higher than the woman's heart rate prior to pregnancy. For some applications, during a calibration phase, a female subject is monitored using sensor 22 before pregnancy. Computer processor receives the sensor signal (step 130), analyzes the sensor signal (step 132), and, based upon the analysis, determines a baseline heart rate (e.g., a baseline average daily heart rate, or a baseline heart rate at a given time period of the day, and/or at a given period of the subject's circadian cycle) for the subject (step 134). Based upon the baseline heart rate, the computer processor determines a pregnancy heart rate measure, which is indicative of what the subject's heart rate is expected to be (e.g., what the average daily heart rate, or the heart rate at a given time period of the day, and/or at a given period of the subject's circadian cycle is expected to be) during a healthy pregnancy (step 136). Typically, the computer processor determines a range of heart rates that are considered to be healthy when the subject is pregnant, based upon the determined baseline heart rate. When the subject is pregnant, during a pregnancy monitoring phase, the computer processor receives the sensor signal (step 138), analyzes the sensor signal (step 140), and based upon the analysis of the signal determines the subject's heart rate (step 142). The computer processor compares the heart rate to the pregnancy heart rate measure that was determined based upon the baseline heart rate (step 144). Based on the comparison, the computer processor determines whether the subject's pregnancy is healthy. For some applications, the computer processor generates an output (e.g., an alert) on an output device (as described hereinabove), in response to the comparison (step 146). For some applications, in response to detecting that the subject's heart rate has returned to the pre-pregnancy baseline heart rate, the computer processor generates an output that is indicative of a recommendation to visit a physician.

Figure 9A:
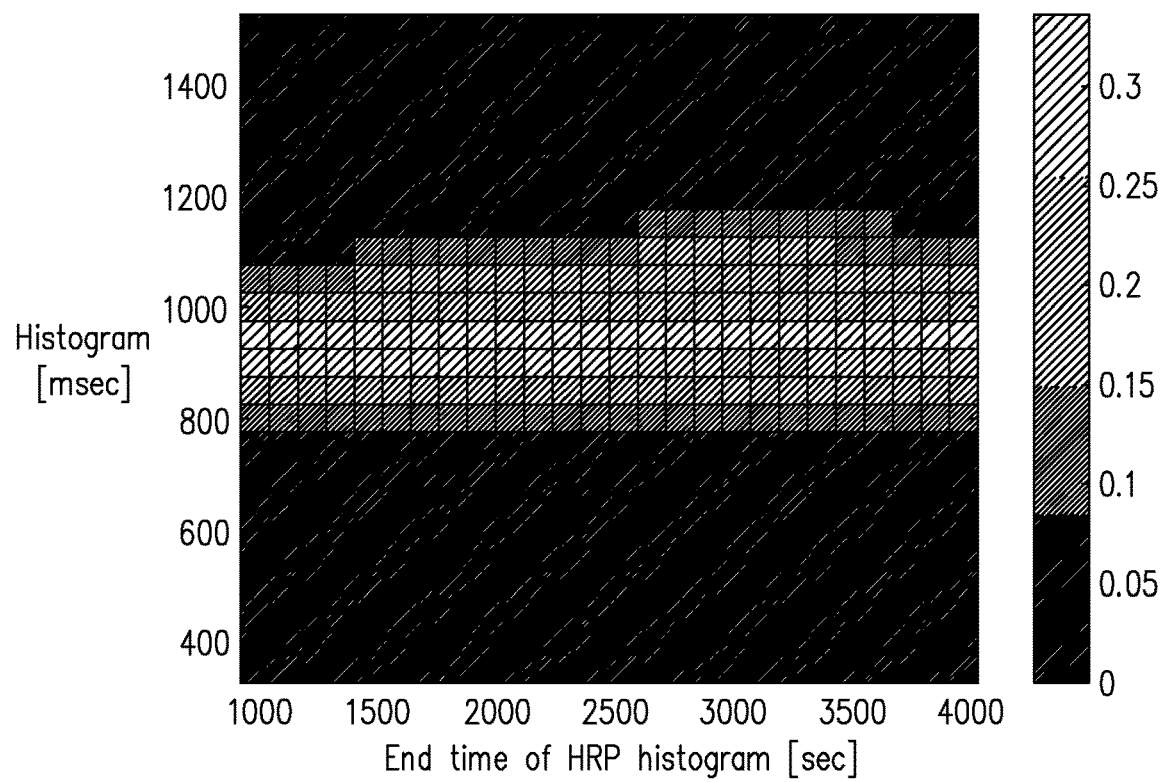
FIGS. 9A-C show histograms of patients' cardiac interbeat intervals that were recorded in accordance with some applications of the present invention.
Figure 9B:
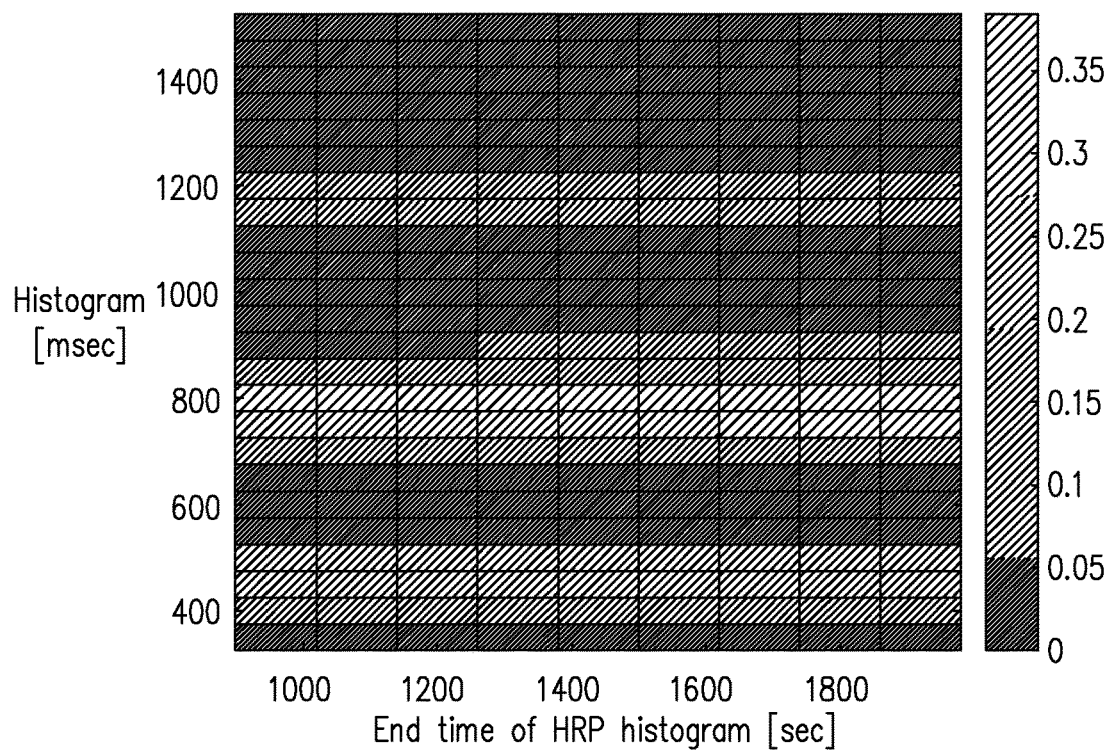
Figure 9C:
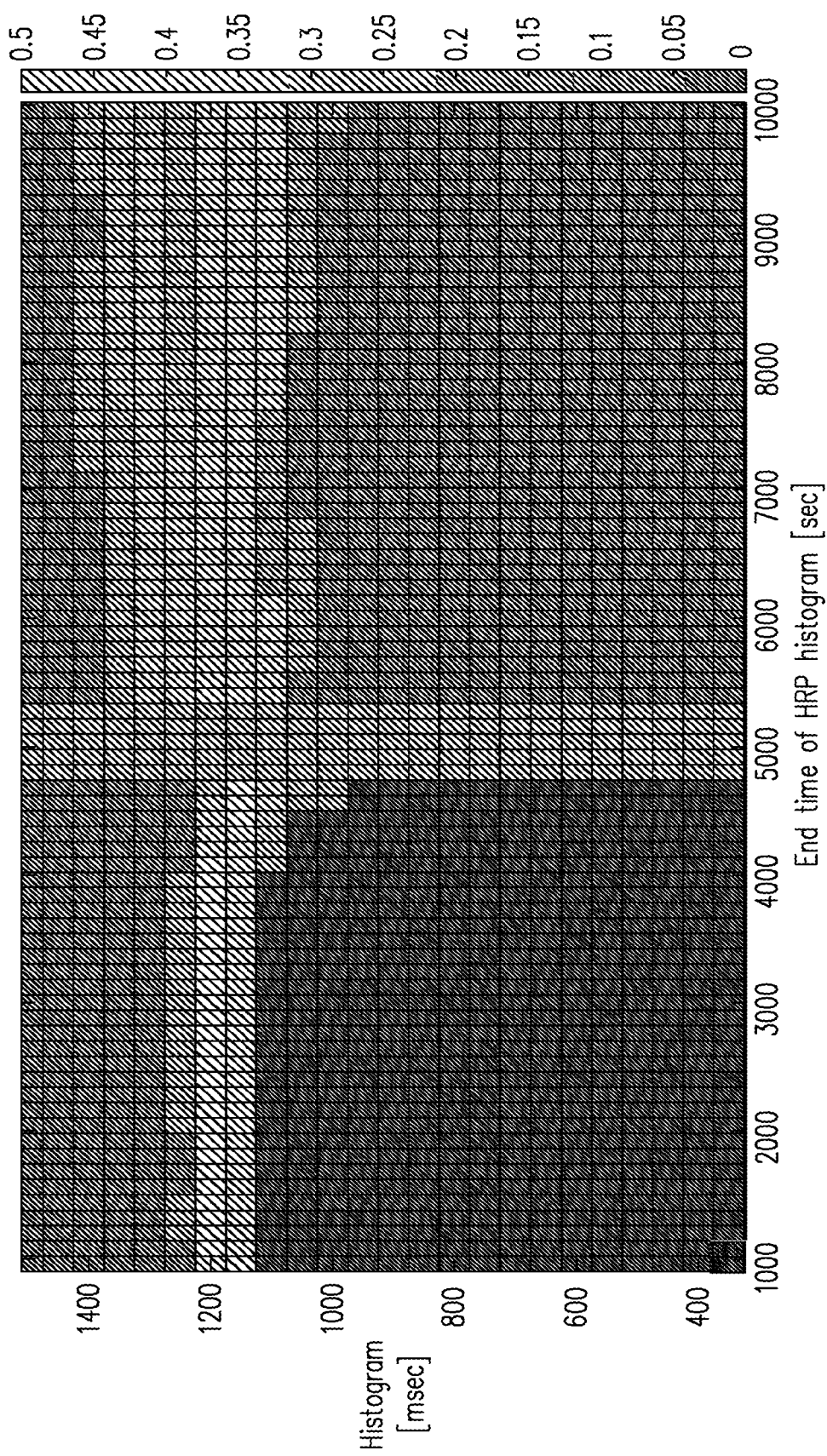

Reference is now made to FIGS. 9A-C, which show histograms of patients' cardiac interbeat intervals that were recorded in accordance with some applications of the present invention. As described hereinabove, for some applications, sensor 22 performs monitoring of the subject without contacting the subject or clothes the subject is wearing, and/or without viewing the subject or clothes the subject is wearing. For some applications, the sensor is configured to detect the subject's cardiac cycle, using techniques as described herein. In some cases, typically due to the non-contact nature of the sensing, some of the subject's heartbeats are not reliably detected. For some such applications, for each heartbeat, the computer processor determines a quality indicator that indicates the quality of the sensed heartbeat. For example, the computer processor may determine the signal-to-noise ratio of the signal, and compare the signal-to-noise ratio to a threshold.

For some applications, the computer processor selects a subset of heartbeats, based upon the qualities of the heartbeats, and some steps of the subsequent analysis (as described herein) are performed only with respect to the subset of heartbeats. For some applications, only in cases in which two consecutive heart beats have a quality indicator that exceeds a threshold, the interbeat interval is calculated and/or is selected for use in subsequent analysis. For some applications, the computer processor builds a histogram of the selected interbeat intervals. The computer processor analyzes the selected interbeat intervals over a period of time, and in response thereto, the computer processor determines whether the subject is healthy or is suffering from arrhythmia, which type of arrhythmia the subject is suffering from, and/or identifies or predicts arrhythmia episodes. For example, the computer processor may build a histogram of the selected interbeat intervals and may perform the above-described steps by analyzing the histogram.

FIGS. 9A-C show sample histograms that were constructed using the above-described technique. The x-axes of the histograms measure the time at which the interbeat interval measurement was recorded, the y-axes measure the interbeat interval and the color legend measures the amplitude of the histogram at each interbeat interval (with a lighter color representing greater amplitude). FIG. 9A shows measurements recorded from a healthy subject, there being only one peak at approximately 900 ms. FIG. 9B is the histogram of an arrhythmic subject, the histogram including two dominant peaks shown by the two light lines at approximately 450 ms and 800 ms. FIG. 9C is the histogram of a subject who starts with a normal cardiac rhythm and at about an x-axis time of 5,500 sec. starts to show an arrhythmia that is manifested by the much wider distribution of the histogram.

In accordance with the above, for some applications, in response to the computer processor identifying two distinct peaks in a histogram that is plotted using the techniques described herein (or performing an equivalent algorithmic operation), an alert is generated that an arrhythmia event may be taking place. Alternatively or additionally, the computer processor may generate an alert in response to identifying that the width of a peak of a histogram exceeds a threshold (or performing an equivalent algorithmic operation). For example, the width of the peak may be compared to a threshold that is determined based upon population averages according to the age and or other indications of the subject (such as, a level of fitness of the subject).

For some applications, in response to the computer processor identifying two distinct peaks in a histogram that is plotted using the techniques described herein (or performing an equivalent algorithmic operation), the computer processor performs the following steps. The computer processor identifies heartbeats belonging to respective interbeat interval groups (i.e., which heartbeats had an interbeat interval that corresponds to a first one of the peaks, and which heartbeats had an interbeat interval corresponding to the second one of the peaks.) The average amplitude of the signal of each of these groups is then calculated. For some applications, the computer processor generates an output that is indicative of the average amplitude of each of the peaks, and/or the interbeat interval of each of the peaks. Alternatively or additionally, based upon these data, the computer processor automatically determines a condition of the subject. For example, the computer processor may determine which category of arrhythmia the subject is suffering from, e.g., atrial fibrillation or ventricular fibrillation.

It is noted that, although the analysis of the interbeat intervals is described as being performed using histogram analysis, the techniques described herein may be combined with other types of analysis that would yield similar results, mutatis mutandis. For example, the computer processor may perform algorithmic steps that do not include a step of generating a histogram, but which analyze the subject's interbeat interval over time, in a similar manner to that described hereinabove.

Figure 10:
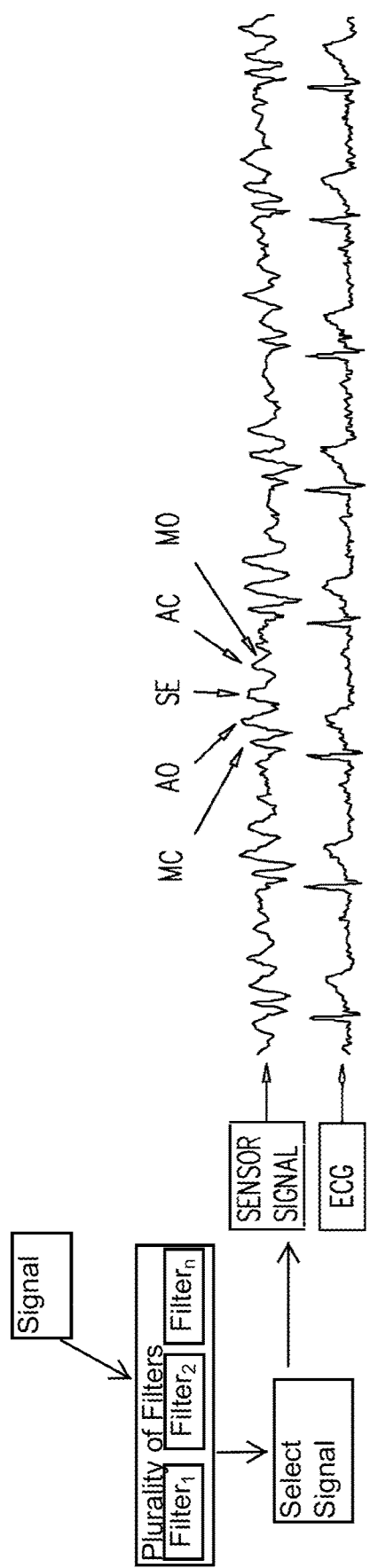
FIG. 10 shows components of a subject's cardiac cycle that were detected in accordance with some applications of the present invention.

Reference is now made to FIG. 10, which shows components of a subject's cardiac cycle that were detected, in accordance with some applications of the present invention. For some applications, sensor 22 is used to monitor a cardiac-related signal of the subject. For some applications, a bank of matched filters with varying filter parameters (e.g., varying width properties) is applied to the raw signal, and one of the filtered signals is selected by the computer processor. For example, the filter having the greatest signalto-noise ratio may be selected, by selecting the filter that generates the highest ratio of the main lobe to the side lobes in the filtered signal. Typically, the filters are designed to have a main lobe with full-width-half-maximum value that fits a human biological beat as recorded with the contact free sensor under the mattress. The bank of filters typically includes filters having a range of relevant full-width-half-maximum values for biological signals. Typically, the filters are zero-mean, e.g., in order to remove any trends, movements or respiration.

Typically, the selection of which filter to use is repeated in response to certain events. For some applications, the selection of a filter is repeated if the signal quality falls below a threshold. Alternatively or additionally, the filter selection is repeated at fixed times intervals (e.g., once every 5 minutes, ten minutes, or 15 minutes). Further, alternatively or additionally, the filter selection is repeated in response to detecting motion of the subject, e.g., large body motion of the subject. For example, in response to the sensor signal indicating that the subject has undergone motion (e.g., large body motion), the computer processor may perform the filter selection.

Referring to FIG. 10, a signal that was detected using the above described technique is shown above the corresponding ECG signal. It may be observed that certain cardiac events, which correlate with the ECG signal, may be extracted from the sensor signal. For example, the following mechanical events can typically be extracted from the sensor signal: mitral valve closure (MC), aortic valve opening (AO), systolic ejection (SE), aortic valve closure (AC), and mitral valve opening (MO). Therefore, for some applications, a cardiac signal that is detected using techniques described herein is analyzed by the computer processor, and one or more of the events are identified. For some applications, in this manner, the computer processor monitors mechanical functioning of the heart. For example, the computer processor may use the identified events to measure the subject's left ventricular ejection time. For some applications, the computer processor analyzes the subject's cardiac cycle, by using the above-described technique in combination with ECG sensing.

In general, computer processor 28 may be embodied as a single computer processor 28, or a cooperatively networked or clustered set of computer processors. Computer processor 28 is typically a programmed digital computing device comprising a central processing unit (CPU), random access memory (RAM), non-volatile secondary storage, such as a hard drive or CD ROM drive, network interfaces, and/or peripheral devices. Program code, including software programs, and data are loaded into the RAM for execution and processing by the CPU and results are generated for display, output, transmittal, or storage, as is known in the art. Typically, computer processor 28 is connected to one or more sensors via one or more wired or wireless connections. Computer processor 28 is typically configured to receive signals (e.g., motion signals) from the one or more sensors, and to process these signals as described herein. In the context of the claims and specification of the present application, the term "motion signal" is used to denote any signal that is generated by a sensor, upon the sensor sensing motion. Such motion may include, for example, respiratory motion, cardiac motion, or other body motion, e.g., large body-movement. Similarly, the term "motion sensor" is used to denote any sensor that senses motion, including the types of motion delineated above.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purposes of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 28) coupled directly or indirectly to memory elements (e.g., memory 29) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that each block of the flowcharts shown in FIGS. 3, 4, and 8, and combinations of blocks in the flowcharts, can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 28) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 28 is typically a hardware device programmed with computer program instructions to produce a special purpose computer. For example, when programmed to perform the algorithms described with reference to FIG. 3, computer processor 28 typically acts as a special purpose temperature control computer processor, when programmed to perform the algorithms described with reference to FIG. 4, computer processor 28 typically acts as a special purpose apnea monitoring processor, and when programmed to perform the algorithms described with reference to FIG. 8, computer processor 28 typically acts as a special purpose pregnancy monitoring processor. Typically, the operations described herein that are performed by computer processor 28 transform the physical state of memory 29, which is a real physical article, to have a different magnetic polarity, electrical charge, or the like depending on the technology of the memory that is used.

Techniques described herein may be practiced in combination with techniques described in one or more of the following patents and patent applications, which are incorporated herein by reference. In some applications, techniques and apparatus described in one or more of the following patents and patent applications, which are incorporated herein by reference, are combined with techniques and apparatus described herein:

U.S. patent application Ser. No. 11/048,100, filed Jan. 31, 2005, which issued as U.S. Pat. No. 7,077,810;

U.S. patent application Ser. No. 11/197,786, filed Aug. 3, 2005, which issued as U.S. Pat. No. 7,314,451;

U.S. patent application Ser. No. 11/446,281, filed Jun. 2, 2006, which issued as U.S. Pat. No. 8,376,954;

U.S. patent application Ser. No. 11/552,872, filed Oct. 25, 2006, now abandoned, which published as US 2007/0118054;

U.S. patent application Ser. No. 11/755,066, filed May 30, 2007, now abandoned, which published as US 2008/0114260;

U.S. patent application Ser. No. 11/782,750, filed Jul. 25, 2007, which issued as U.S. Pat. No. 8,403,865;

U.S. patent application Ser. No. 12/113,680, filed May 1, 2008, now abandoned, which published as US 2008/0275349;

U.S. patent application Ser. No. 12/842,634, filed Jul. 23, 2010, which issued as U.S. Pat. No. 8,517,953;

U.S. patent application Ser. No. 12/938,421, filed Nov. 3, 2010, which issued as U.S. Pat. No. 8,585,607;

U.S. patent application Ser. No. 12/991,749, filed Nov. 9, 2010, which issued as U.S. Pat. No. 8,821,418;

U.S. patent application Ser. No. 13/107,772, filed May 13, 2011, which issued as U.S. Pat. No. 8,491,492;

U.S. patent application Ser. No. 13/305,618, filed Nov. 28, 2011, now abandoned, which published as US 2012/0132211;

U.S. patent application Ser. No. 13/389,200, filed Jun. 13, 2012, now abandoned, which published as US 2012/0253142;

U.S. patent application Ser. No. 13/750,957, filed Jan. 25, 2013, which issued as U.S. Pat. No. 8,603,010;

U.S. patent application Ser. No. 13/750,962, filed Jan. 25, 2013, which issued as U.S. Pat. No. 8,679,034;

U.S. patent application Ser. No. 13/863,293, filed Mar. 15, 2013, now abandoned, which published as US 2013/0245502;

U.S. patent application Ser. No. 13/906,325, filed May 30, 2013, which issued as U.S. Pat. No. 8,882,684;

U.S. patent application Ser. No. 13/921,915, filed Jun. 19, 2013, which issued as U.S. Pat. No. 8,679,030;

U.S. patent application Ser. No. 14/019,371, filed Sep. 5, 2013, which published as US 2014/0005502;

U.S. patent application Ser. No. 14/020,574, filed Sep. 6, 2013, which issued as U.S. Pat. No. 8,731,646;

U.S. patent application Ser. No. 14/054,280, filed Oct. 15, 2013, which issued as U.S. Pat. No. 8,734,360;

U.S. patent application Ser. No. 14/150,115, filed Jan. 8, 2014, which issued as U.S. Pat. No. 8,840,564;

U.S. patent application Ser. No. 14/231,855, filed Apr. 1, 2014, which issued as U.S. Pat. No. 8,992,434;

U.S. patent application Ser. No. 14/454,300, filed Aug. 7, 2014, which issued as U.S. Pat. No. 8,942,779;

U.S. patent application Ser. No. 14/458,399, filed Aug. 13, 2014, which issued as U.S. Pat. No. 8,998,830;

U.S. patent application Ser. No. 14/474,357, filed Sep. 2, 2014, which published as US 2014/0371635;

U.S. patent application Ser. No. 14/557,654, filed Dec. 2, 2014, issued as U.S. Pat. No. 9,026,199;

U.S. patent application Ser. No. 14/631,978, filed Feb. 26, 2015, published as US 2015/0164438;

U.S. patent application Ser. No. 14/624,904, filed Feb. 18, 2015, published as US 2015/0164433;

U.S. patent application Ser. No. 14/663,835, filed Mar. 20, 2015, published as US 2015/0190087;

U.S. patent application Ser. No. 14/810,814, filed Jul. 28, 2015, published as US 2015/0327792;

International Patent Application PCT/IL2005/000113, which published as WO 2005/074361;

International Patent Application PCT/IL2006/000727, which published as WO 2006/137067;

International Patent Application PCT/IB2006/002998, which published as WO 2007/052108;

International Patent Application PCT/IL2008/000601, which published as WO 2008/135985;

International Patent Application PCT/IL2009/000473, which published as WO 2009/138976;

International Patent Application PCT/IL2011/050045, which published as WO 2012/077113;

International Patent Application PCT/IL2013/050283, which published as WO 2013/150523;

International Patent Application PCT/IL2014/050644, which published as WO 2015/008285; and International Patent Application No. PCT/IL2015/050880 to Shinar, which published as WO 16/035073.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for monitoring a subject, the apparatus comprising:

a sensor, configured to monitor the subject and to generate a sensor signal in response thereto; and a computer processor, configured to:
receive the sensor signal,
filter the signal with each of a plurality of filters configured to filter the sensor signal using respective filter parameters to create respective filtered signals,
in response to a first respective quality of each of the filtered signals, select one of the plurality of filters to filter the sensor signal, and
subsequently:
detect that the subject has undergone motion, by analyzing the sensor signal,
in response thereto, re-filter the signal with each of two or more of the plurality of filters, and in response to a second respective quality of each of the re-filtered signals, select one of the plurality of filters to filter the sensor signal.

2. The apparatus according to claim 1, wherein the sensor is configured to monitor a cardiac-related signal of the subject.

3. The apparatus according to claim 1, wherein the plurality of filters are configured to filter the sensor signal using respective bandwidth properties.

4. The apparatus according to claim 1, wherein the plurality of filters are zero-mean filters.

5. The apparatus according to claim 4, wherein the filters are configured to remove any trends, movements of the subject, or respirations of the subject.

6. The apparatus according to claim 1, wherein the sensor is a contact-free sensor disposed on or within the subject's bed.

7. The apparatus according to claim 6, wherein the sensor is configured to be disposed underneath the subject's mattress.

8. The apparatus according to claim 7, wherein the plurality of filters are configured to have a main lobe with a full-width-half-maximum value corresponding to a human biological heartbeat as recorded with the contact free sensor under the subject's mattress.

9. The apparatus according to claim 1, wherein the computer processor is configured to select the one of the plurality of filters to filter the sensor signal by selecting the filter having the greatest signal-to-noise ratio.

10. The apparatus according to claim 9, wherein the computer processor is configured to select the filter having the greatest signal-to-noise ratio by selecting the filter that generates the highest ratio of the main lobe to the side lobes in the filtered signal.

11. The apparatus according to claim 1, wherein the computer processor is further configured to:
detect if the signal quality falls below a threshold,
in response thereto, filter the signal with each of two or more of the filters, and
in response to a quality of each of the filtered signals, select one of the plurality of filters to filter the sensor signal.

12. The apparatus according to claim 1, wherein the computer processor is further configured to, at fixed time intervals, filter the signal with each of two or more of the filters and in response to a quality of each of the filtered signals, select one of the plurality of filters to filter the sensor signal.

13. The apparatus according to claim 12, wherein the computer processor is configured to, every 5 minutes, filter the signal with each of two or more of the filters and in response to a quality of each of the filtered signals, select one of the plurality of filters to filter the sensor signal.

14. The apparatus according to claim 12 wherein the computer processor is configured to, every 10 minutes, filter the signal with each of two or more of the filters and in response to a quality of each of the filtered signals, select one of the plurality of filters to filter the sensor signal.

15. The apparatus according to claim 12, wherein the computer processor is configured to, every 15 minutes, filter the signal with each of two or more of the filters and in response to a quality of each of the filtered signals, select one of the plurality of filters to filter the sensor signal.

16. The apparatus according to claim 1, wherein the apparatus is configured to be used in combination with an electrocardiography (ECG) signal, and wherein the sensor is configured to monitor a cardiac-related signal of the subject, and the computer processor is further configured to analyze the sensor signal and in response thereto extract one or more cardiac events which correlated with the ECG signal, the one or more cardiac events selected from the group consisting of: mitral valve closure, aortic valve opening, systolic ejection, aortic valve closure, and mitral valve opening.

17. The apparatus according to claim 16, wherein the computer processor is configured to use the identified one or more events to monitor mechanical functioning of the subject's heart.

18. The apparatus according to claim 17, wherein the computer processor is configured to use the identified one or more events to measure the subject's left ventricular ejection time.

19. The apparatus according to claim 16, wherein the computer processor is configured to, in combination with the ECG signal, use the identified one or more events to analyze the subject's cardiac cycle.

20. The apparatus according to claim 1, wherein the processor selects a subset of filters based upon the first respective quality of each of the filtered signals, and wherein when the subject has undergone motion, the processor re-filters the signal with each of two or more of the plurality of filters selected from the subset of filters.

* * * * *